United States Patent [19]
Clark et al.

[11] Patent Number: 5,724,305
[45] Date of Patent: Mar. 3, 1998

[54] APPARATUS FOR ACOUSTIC NEAR FIELD SCANNING USING CONFORMAL ARRAYAL

[75] Inventors: Joseph A. Clark; Michael A. Sartori, both of Arlington, Va.; Moon H. Cho, Fairfax; Daniel F. Dozier, Vienna, all of Va.

[73] Assignee: The United States of America as represented by the Secretary of the Navy, Washington, D.C.

[21] Appl. No.: 497,591

[22] Filed: Jun. 30, 1995

[51] Int. Cl.⁶ .................................................. H04B 17/00
[52] U.S. Cl. ................................................. 367/13
[58] Field of Search ........................... 367/13, 135, 140; 73/633, 634, 640

[56] References Cited

U.S. PATENT DOCUMENTS

| | | | |
|---|---|---|---|
| 4,102,204 | 7/1978 | Kretz | 73/626 |
| 4,660,419 | 4/1987 | Derkacs et al. | 73/622 |
| 4,704,614 | 11/1987 | Poirer et al. | 343/703 |
| 4,957,000 | 9/1990 | Delpy et al. | 73/622 |
| 5,007,291 | 4/1991 | Walters et al. | 73/640 |
| 5,319,375 | 6/1994 | Gallergo et al. | 342/360 |
| 5,347,496 | 9/1994 | Clark et al. | 367/140 |
| 5,365,241 | 11/1994 | Williams et al. | 343/703 |
| 5,381,381 | 1/1995 | Sartori et al. | 367/1 |
| 5,648,936 | 7/1997 | Clark et al. | 367/13 |

*Primary Examiner*—Daniel T. Pihulic
*Attorney, Agent, or Firm*—Howard Kaiser

[57] ABSTRACT

Acoustic near field measurement apparatus uniquely featuring mechanical economy, in terms of placement and motion of one or more acoustic measurement devices, which is accorded by the geometric character of a structure having indicia of symmetry. One or more devices are arranged, and/or caused to move with up to three degrees of freedom, so as to manifest conformance with respect to the surface of the structure. If desired, virtually complete acoustic near field mapping of the structure can be effectuated. Examples of the various embodiments of this invention include: circumferentially conformal arrayal of devices in combination with longitudinal movement of the arrayal; longitudinally conformal arrayal of devices in combination with circumferential movement of the arrayal; movement of one or more devices in a path or paths which are circumferentially conformal; movement of one or more devices in a path or paths which are longitudinally conformal; movement of one or more devices in a path or paths which are radial. For some embodiments a single device can be caused to move circumferentially, longitudinally and radially, and thus is provided three degrees of freedom. The apparatus according to this invention is more feasible and reliable than previous apparatus, especially for larger structures.

32 Claims, 15 Drawing Sheets

APPARATUS FOR ACOUSTIC NEAR FIELD SCANNING USING CONFORMAL ARRAYAL

The invention described herein may be manufactured and used by or for the Government of the United States of America for governmental purposes without the payment of any royalties thereon or therefor.

This application is related to U.S. patent application Ser. No. 08/497,589, filed 30 Jun. 1995, now U.S. Pat. No. 5,648,936, entitled "Method for Acoustic Near Field Scanning Using Conformal Arrayal," inventors Joseph A. Clark and Michael A. Sartori.

BACKGROUND OF THE INVENTION

The present invention relates to acoustic measurement, more particularly to method and apparatus for measuring the acoustic near field of a structure.

The term "acoustic near field" refers to the area of a structure where both radiating and non-radiating (i.e., evanescent) acoustic waves exist. The term "acoustic far field" refers to the area around a structure where only the radiating acoustic waves exist and the non-radiating acoustic waves have decayed.

For a given structure producing radiating and non-radiating waves, the radiating waves produce observable responses in the acoustic far field while the non-radiating acoustic waves do not. In mapping the acoustic near field of the structure, both the radiating and the non-radiating acoustic waves are measured. Using this technique, information on the types of structural waves traveling along the structure and their contribution to the observable responses in the acoustic far field can be obtained.

Three basic measurement approaches have been conventionally employed for mapping the acoustic near field of a structure, viz.: (i) moving the structure with respect to a stationary scanning system; (ii) moving a scanning system with respect to the stationary structure; and, (iii) surrounding the structure with a multitude of acoustic measurement devices which are included in the scanning system.

In accordance with the first two conventional approaches, the scanning system includes an array of acoustic measurement devices; either the structure is moved or the array of acoustic measurement devices is moved. Frequently, the array of acoustic measurement devices for these conventional techniques is a linear array or a planar array.

Application of the first approach to a larger structure (e.g., a structure occupying a rectangular region of the size 30'×30'×180') may be impractical, as moving the structure may become unwieldy; moreover, difficulties may arise in maintaining the appropriate distance between the acoustic measurement devices and the moving structure.

Application of the second approach has also had its practical difficulties for larger structures. The conventional technique of mounting acoustic measurement devices on a computer-controlled robot arm can readily measure the acoustic near field of a small structure (e.g., a structure occupying a rectangular region of the size 0.5'×0.5'×3.0'); however, the same robot arm may be found to be inappropriate for a larger version of the structure, and the expense and effort for building a scaled-up version of the robot arm may be prohibitive.

According to the third conventional technique, the scanning system includes acoustic measurement devices located at all positions where measurements of the acoustic near field are desired. The advantage of this technique vis-a-vis' the first two conventional techniques is that neither the structure nor the acoustic measurement devices need be moved; however, this third conventional technique often requires implementation of numerous acoustic measurement devices, which may be forbiddingly costly. Furthermore, utilizing this technique so as to place acoustic measurement devices at numerous locations and thereby conduct a "full array" covering of a structure has been known to result in distortion of the acoustic near field being measured.

Clark and Sartori at U.S. Pat. No. 5,347,496, issued 13 Sep. 1994, incorporated herein by reference, disclose mapping of the acoustic near field of an axially symmetrical structure whereby the structure is subjected to excitation energy along one or more lines which are longitudinally conformal with the surface of the structure.

SUMMARY OF THE INVENTION

In view of the foregoing, it is an object of the present invention to provide method and apparatus for measuring the acoustic near field of a structure which are more practical and efficient than conventional methods, especially for larger structures, including larger submerged structures.

It is a further object of this invention to provide such method and apparatus which are more reliable than conventional methods.

Another object of the present invention to provide such method and apparatus which are more economical than conventional methods.

A further object of this invention to provide such method and apparatus which admit of portabillity.

The present invention provides improved method and apparatus for scanning the acoustic near field of a structure having a circumferential surface about its longitudinal axis. Featured by this invention is the recognition that axially symmetrical shapes uniquely lend themselves to surface mapping by means of certain economies of movement of acoustic measurement devices.

This invention novelly improves upon the aforementioned conventional acoustic near field measurement methodologies by bringing to bear fundamental principles of solid geometry. Repeated and systematic measurement effectuation in accordance with this invention permits substantially or virtually complete mapping of the acoustic near field of the structure. The measurements according to this invention are taken "conformally" with respect to a structure, pursuant to fundamental principles of geometric proportionality and similarity.

Moreover, the measurements in accordance with the present invention are performed so as to minimize the number of degrees of freedom of movement of the mechanical system for a measurement device or an array of measurement devices, thereby maximizing efficiency and minimizing the number of variables associated with performing such measurements, and hence minimizing the number of factors that can create error in performing such measurements.

Thus, measurements performed according to the present invention have greater indicia of reliability in terms of consistency and uniformity of their distance and relation with respect to the structure. The heightened measurement dependability which accompanies practice of the present invention becomes increasingly manifest as the acoustic near field scanning of the structure approaches completeness. For embodiments of the present invention such as "belt-driven" embodiments described hereinbelow with reference to FIG. 18 and FIG. 19, the measuring of the acoustic near field of a structure is accomplished using an acoustically isolated scanning system which is in physical contact with the structure; this approach greatly reduces the placement uncertainty involved when the scanning system and the structure are not physically joined.

In addition, the mathematical purity and mechanical efficiency of the present invention carry significant economic advantage. Acoustic measurement devices are typically expensive; practice of the present invention requires use of far fewer acoustic measurement devices than do conventional acoustic near field measurement approaches in general. Most embodiments of the method according to this invention involve apparatus which is portable and inexpensive to build and assemble, resulting in substantial savings and especially so when studying larger structures which cannot be easily transported.

Some conventional approaches to mapping the acoustic near field involve placement of acoustic measurement devices at numerous locations around the structure. Exorbitant costs concomitant with design, procurement and construction of a "full array" measurement methodology for a given structure will normally not be incurred in practicing the present invention. Moreover, such "full array" covering of the structure has been known to distort the acoustic near field to be measured. This character of distortion does not occur in accordance with the present invention.

In accordance with this invention, neither the structure nor the scanning system needs to be physically rotated, which is a difficult and/or costly proposition for most structures. Practice of the present invention for large structures is considerably more economical vis-a-vis' a conventional approach of building a robot arm to study the same large structures. The measuring of the acoustic near field of structures, according to this invention, can be accomplished using an acoustically isolated and acoustically transparent scanning system. For some embodiments of this invention, with utilization of computer-controlled precise stepping motors to position one or more acoustic measurement devices (e.g., sensors), an extremely accurate positioning system can be obtained.

Accordingly, the method and apparatus according to the present invention implement a simple mechanical system which geometrically "conforms" with a structure so as to effectuate more efficient, more economical and more accurate acoustic near field measurements of the structure. According to this invention, a mechanical system of one or more acoustic measurement devices has one, two or three degrees of freedom. The three possible degrees of freedom according to this invention are (i) longitudinal movability, (ii) circumferential movability, and (iii) radial movability.

"Movable conformal array" embodiments according to this invention, which comprise "movable conformal ring array" embodiments and "movable conformal line array" embodiments, have one degree of freedom. A "movable conformal ring array" embodiment includes a circumferentially conformal array of devices; the circumferentially conformal array is (i) longitudinally movable. A "movable conformal line array" embodiment includes a longitudinally conformal array of devices; the longitudinally conformal array is (ii) circumferentially movable.

"Conformal path" embodiments according to this invention comprise "conformal ring path" embodiments and "conformal line path" embodiments. "Stationary conformal path" embodiments according to this invention, which comprise "stationary conformal ring path" embodiments and "stationary conformal line path" embodiments, have one degree of freedom. A "stationary conformal ring path" embodiment includes a device which is (ii) movable in a stationary circumferentially conformal path. A "stationary conformal line path" embodiment includes a device which is (i) movable in a stationary longitudinally conformal path.

"Movable conformal path" embodiments according to this invention, which comprise "movable conformal ring path" embodiments and "movable conformal line path" embodiments, have two degrees of freedom. A "movable conformal ring path" embodiment includes a device which is (ii) movable in a circumferentially conformal path; the circumferentially conformal path is (i) longitudinally movable. A "movable conformal line path" embodiment includes a device which is (i) movable in a longitudinally conformal path; the longitudinally conformal path is (ii) circumferentially movable.

"Radially adjustable conformal array" embodiments according to this invention, which comprise "radially adjustable conformal ring array" embodiments and "radially adjustable conformal line array" embodiments, have two degrees of freedom. A "radially adjustable conformal ring array" embodiment includes a circumferentially conformal array of devices; the circumferentially conformal array is (i) longitudinally movable and (iii) radially movable. A "radially adjustable conformal line array" embodiment includes a longitudinally conformal array of devices; the longitudinally conformal array is (ii) circumferentially movable and (iii) radially movable.

"Radially adjustable conformal path" embodiments, which include "radially adjustable conformal ring path" embodiments and "radially adjustable conformal line path" embodiments, have two or three degrees of freedom. "Radially adjustable conformal path" embodiments include "radially adjustable stationary conformal path" embodiments and "radially adjustable movable conformal path" embodiments.

"Radially adjustable stationary conformal path" embodiments, which include "radially adjustable stationary conformal ring path" embodiments and "radially adjustable stationary conformal line path" embodiments, have two degrees of freedom. A "radially adjustable stationary conformal ring path" embodiment includes a device which is (ii) movable in a stationary circumferentially conformal path and which is (iii) radially movable. A "radially adjustable stationary conformal line path" embodiment includes a device which is (i) movable in a stationary longitudinally conformal path and which is (iii) radially movable.

"Radially adjustable movable conformal path" embodiments, which include "radially adjustable movable conformal ring path" embodiments and "radially adjustable movable conformal line path" embodiments, have three degrees of freedom. A "radially adjustable movable conformal ring path" embodiment includes a device which is (ii) movable in a circumferentially conformal path and which is (iii) radially movable; the circumferentially conformal path is (i) longitudinally movable. A "radially adjustable movable conformal line path" embodiment includes a device which is (i) movable in a longitudinally conformal path and which is (iii) radially movable; the longitudinally conformal path is (ii) circumferentially movable.

A "conformal ring array" according to this invention is an arrangement of a plurality of acoustic measurement devices which conforms with the surface of a structure in the structure's circumferential direction. In practicing this invention the "movable conformal ring array" is provided with one degree of freedom, i.e., in the longitudinal direction. The conformal ring array is moved to selected locations along the longitudinal axis and the acoustic near field is appropriately measured at each location.

A "conformal line array," according to this invention is an arrangement of a plurality of acoustic measurement devices which conforms with the surface of a structure in the structure's longitudinal direction. In practicing this invention the "movable conformal line array" is provided with one degree of freedom, i.e., in the circumferential direction. The conformal line array is moved to selected locations around the circumference and the acoustic near field is appropriately measured at each location.

A "conformal path" according to this invention is either a "conformal ring path" or a "conformal line path". "Conformal path" embodiments provide one degree of freedom for an acoustic measurement device within a prescribed path. According to "movable conformal path" embodiments, the path itself is provided one degree of freedom; hence, the device has two degrees of freedom.

For "movable conformal ring path" embodiments, movability of the device in a circumferentially conformal path is combined with longitudinal movability of the path; the device is moved in a path which conforms with the surface of the structure in the structure's circumferential direction, and the path is moved in the structure's longitudinal direction.

For "movable conformal line path" embodiments, movability of the device in a longitudinally conformal path is combined with circumferential movability of the path; the device is moved in a path which conforms with the surface of the structure in the structure's longitudinal direction, and the path is moved in the structure's circumferential direction.

"Radially adjustable conformal array" embodiments and "radially adjustable conformal path" embodiments add the dimension of radial movability to "conformal array" embodiments and "conformal path" embodiments, respectively. A "radially adjustable conformal array" embodiment provides radial movability of a "conformal array." In practice of this invention, "radial adjustability" of a "conformal line array" may be more feasible than "radial adjustability" of a "conformal ring array," and hence may be more highly recommended for most applications.

"Radially adjustable conformal path" embodiments of this invention provide radial movability of a device which moves in a "conformal path." A "conformal path" embodiment can be imparted "radial adjustability" according to some "radially adjustable conformal path" embodiments of this invention by providing radial movability for the conformal path itself rather than for the device which moves in the conformal path; however, for most "radial adjustable conformal path" embodiments, providing radial movability for the device itself may make more practical sense.

A "belt-driven" embodiment of this invention comprises at least one toothed belt whereby each belt either circumferentially or longitudinally contacts the structure, gearing means which meshes with each said belt, and stepping motor means which turns the gearing means.

A "rack-and-pinion driven" embodiment of this invention comprises at least one rack-like track whereby each track is either circumferentially (e.g., encirclingly) adjacent or longitudinally adjacent or radially adjacent the structure, pinion-like gearing means which meshes with each track, and stepping motor means which turns the gearing means.

The term "structure having a circumferential surface about its longitudinal axis," as used herein, refers not only to a structure having a curvilinear surface which is axially symmetrical about a longitudinal axis, but also refers to a structure having a generally curvilinear surface or a substantially curvilinear surface which is generally symmetrical or substantially symmetrical about a longitudinal axis.

Although the method and apparatus according to this invention admit of application to structures having aspects of asymmetricality and rectilinearity, many applications thereof are for axially symmetrical structures such as circular cylinders, non-circular (e.g., elliptical) cylinders, circular cones, non-circular (e.g., elliptical) cones, spheres, prolate spheres, circular spheroids, non-circular (e.g., elliptical) spheroids, circular ellipsoids and non-circular (e.g., elliptical) ellipsoids. The circumferential planar cross-sections for these axially symmetrical structures are circular or elliptical. Many structures for which the present invention may be practiced have shapes which are substantial or general analogues of these axially symmetrical shapes. Even rectangular and other entirely rectilinear structural shapes admit of practice in accordance with the present invention, provided an axis of virtual symmetry for the structure can be identified and appropriate conformity with the structure's surface can be achieved.

Accordingly, for "conformal ring array" embodiments, the present invention provides method and apparatus for scanning the acoustic near field of a structure having a circumferential surface about its longitudinal axis. The method comprises providing a frame for the structure, engaging at least one array of acoustic measurement devices with respect to the frame whereby each array is approximately conformal with respect to the surface in the circumferential direction and is movable in the longitudinal direction, at least twice positioning each array, and measuring the acoustic near field upon each positioning of each array. The apparatus comprises a frame for the structure, at least one array of acoustic measurement devices, means for engaging each array with respect to the frame so as to be approximately conformal with respect to the surface in the circumferential direction and movable in the longitudinal direction, and means for intermittently driving each array in the longitudinal direction.

For "conformal ring array" embodiments" which are radially adjustable conformal ring array" embodiments, the method according to this invention further comprises engaging at least one array with respect to the frame whereby the array is movable in the radial direction, and the apparatus according to this invention further comprises means for engaging at least one array with respect to the frame whereby the array is movable in the radial direction.

For "conformal line array" embodiments, the present invention provides method and apparatus for scanning the acoustic near field of a structure having a circumferential surface about its longitudinal axis. The method comprises providing a frame for the structure, engaging at least one array of acoustic measurement devices with respect to the frame whereby each array is approximately conformal with respect to the surface in the longitudinal direction and is movable in the circumferential direction, at least twice positioning each array, and measuring the acoustic near field upon each positioning of each array. The apparatus comprises a frame for the structure, at least one array of acoustic measurement devices, means for engaging each array with respect to the frame so as to be approximately conformal with respect to the surface in the longitudinal direction and movable in the circumferential direction, and means for intermittently driving each array in the circumferential direction.

For "conformal line array" embodiments which are "radially adjustable conformal line array" embodiments, the method according to this invention further comprises engaging the array with respect to the frame whereby at least one array is movable in the radial direction, and the apparatus according to this invention further comprises means for engaging at least one array with respect to the frame whereby the array is movable in the radial direction.

For "conformal ring path" embodiments which are "stationary conformal ring path" embodiments, the present invention provides method and apparatus for scanning the acoustic near field of a structure having a circumferential surface about its longitudinal axis. The method comprises providing a frame for the structure, engaging at least one acoustic measurement device with respect to the frame whereby each device is movable in a corresponding path which is approximately conformal with respect to the surface in the circumferential direction, positioning each device at least twice, and measuring the acoustic near field upon each positioning of each device. The apparatus comprises a frame for the structure, at least one acoustic measurement device, means for engaging each device with respect to the frame so as to be movable in a corresponding path which is approximately conformal with respect to the surface in the circumferential direction, and means for intermittently driving each device in the circumferential direction.

For "stationary conformal ring path" embodiments which are "radially adjustable stationary conformal ring path" embodiments, the method according to this invention further comprises engaging at least one device with respect to the frame whereby the device is movable in the radial direction, and the apparatus according to this invention further comprises means for engaging at least one device with respect to the frame whereby the device is movable in the radial direction.

For "conformal ring path" embodiments which are "movable conformal ring path" embodiments, the method according to this invention further comprises engaging at least one device with respect to the frame whereby the device is movable in the longitudinal direction, and the apparatus according to this invention further comprises means for engaging at least one device with respect to the frame whereby the device is movable in the longitudinal direction.

For "movable conformal ring path" embodiments which are "radially adjustable movable conformal ring path" embodiments, the method according to this invention further comprises engaging at least one device with respect to the frame whereby the device is movable in the longitudinal direction and in the radial direction.

For "conformal line path" embodiments which are "stationary conformal line path" embodiments, the present invention provides method and apparatus for scanning the acoustic near field of a structure having a circumferential surface about its longitudinal axis. The method comprises providing a frame for the structure, engaging at least one acoustic measurement device with respect to the frame whereby each device is movable in a corresponding path which is approximately conformal with respect to the surface in the longitudinal direction, positioning each device at least twice, and measuring the acoustic near field upon each positioning of each device. The apparatus comprises a frame for the structure, at least one acoustic measurement device, means for engaging each device with respect to the frame so as to be movable in a corresponding path which is approximately conformal with respect to the surface in the longitudinall direction, and means for intermittently driving each device in the longitudinalal direction.

For "stationary conformal line path" embodiments which are "radially adjustable stationary conformal line path" embodiments, the method according to this invention further comprises engaging at least one device with respect to the frame whereby the device is movable in the radial direction, and the apparatus according to this invention further comprises means for engaging at least one device with respect to the frame whereby the device is movable in the radial direction.

For "conformal line path" embodiments which are "movable conformal line path" embodiments, the method according to this invention further comprises engaging at least one device with respect to the frame whereby the device is movable in the circumferential direction, and the apparatus according to this invention further comprises means for engaging at least one device with respect to the frame whereby the device is movable in the circumferential direction.

For "movable conformal line path" embodiments which are "radially adjustable movable conformal line path" embodiments, the method according to this invention further comprises engaging at least one device with respect to the frame whereby the device is movable in the circumferential direction and in the radial direction.

Other objects, advantages and features of this invention will become apparent from the following detailed description of the invention when considered in conjunction with the accompanying drawings.

BRIEF DESCRIPTION OF THE DRAWINGS

In order that the present invention may be clearly understood, it will now be described by way of example, with reference to the accompanying drawings, wherein like numbers indicate the same or similar components, and wherein.

DETAILED DESCRIPTION OF THE INVENTION

Figure 1:
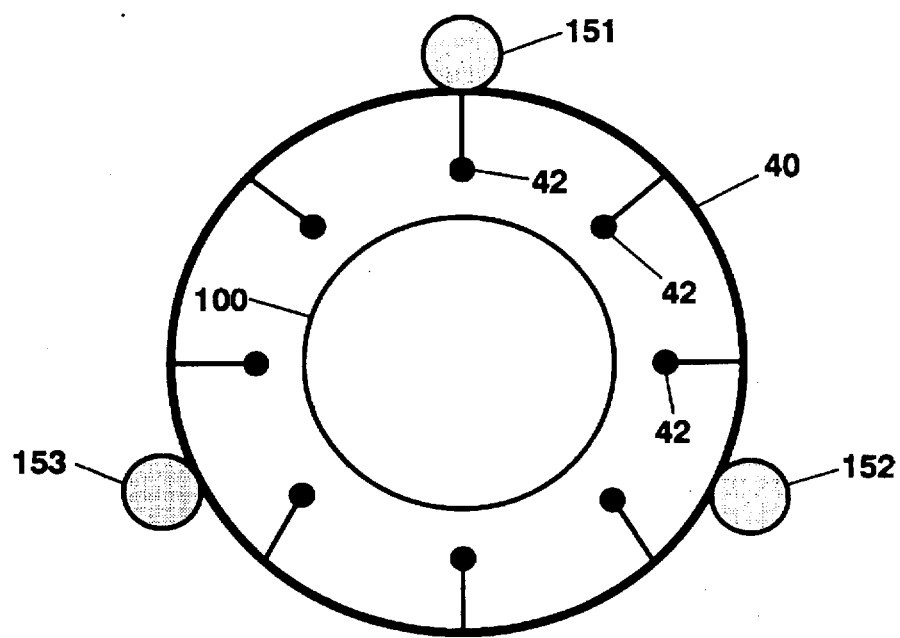
FIG. 1 is a diagrammatic end elevational view of a "movable conformal ring array" embodiment of method and apparatus for scanning the acoustic near field of a structure in accordance with the present invention, wherein the structure is cylindrical.
Figure 2:
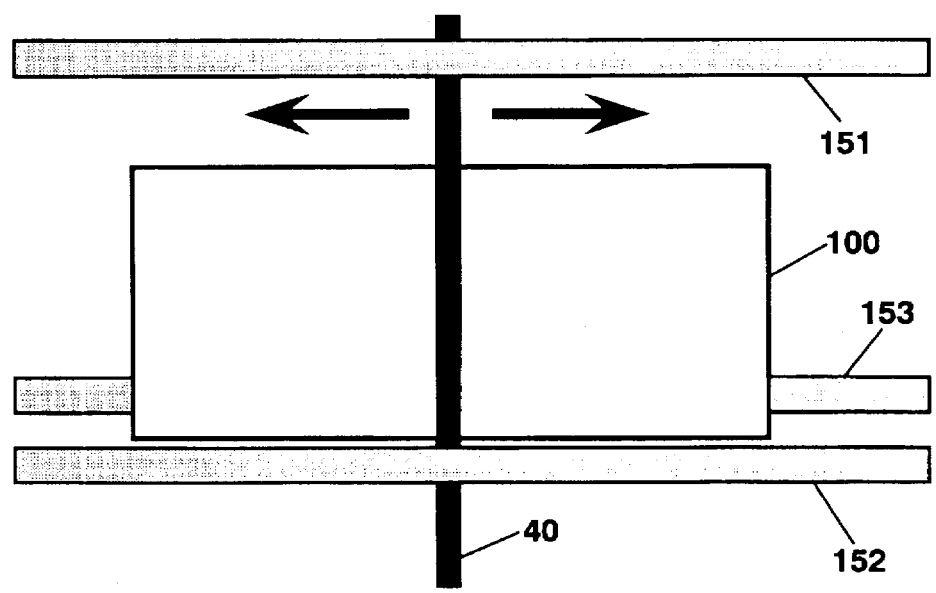
FIG. 2 is a diagrammatic side elevational view, slightly in perspective, of the embodiment shown in FIG. 1.

Referring now to FIG. 1 and FIG. 2, conformal ring array 40 of acoustic measurement devices 42 is placed around cylindrical structure 100. Acoustic measurement devices such as, but not limited to, hydrophones and microphones, are well known in the art. In FIG. 1 eight acoustic measurement devices 42 are shown symmetrically positioned about conformal ring array 40.

With particular reference to FIG. 2, in which acoustic measurement devices 42 are not shown, conformal ring array 40 longitudinally traverses structure 100. Conformal ring array 40 is moved longitudinally along structure 100 guided by a scanning frame, which is represented in FIG. 1 and FIG. 2 by longitudinal supports 151, 152 and 153. The scanning frame is constructed of an acoustically transparent material. For example, PVC pipe could be used for underwater acoustic testing.

Figure 3:
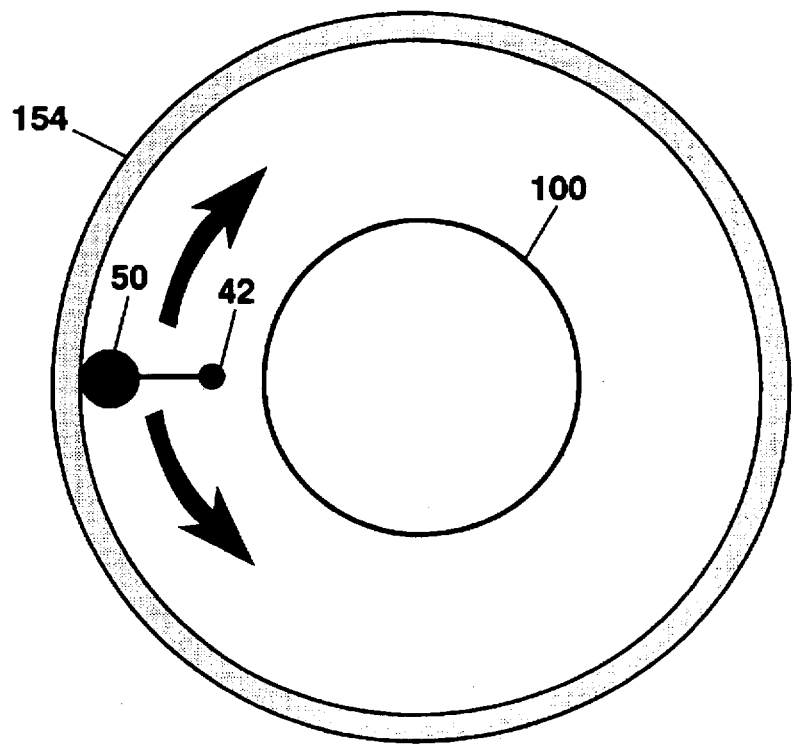
FIG. 3 is a diagrammatic end elevational view of a "movable conformal line array" embodiment in accordance with the present invention, wherein the structure is cylindrical.
Figure 4:
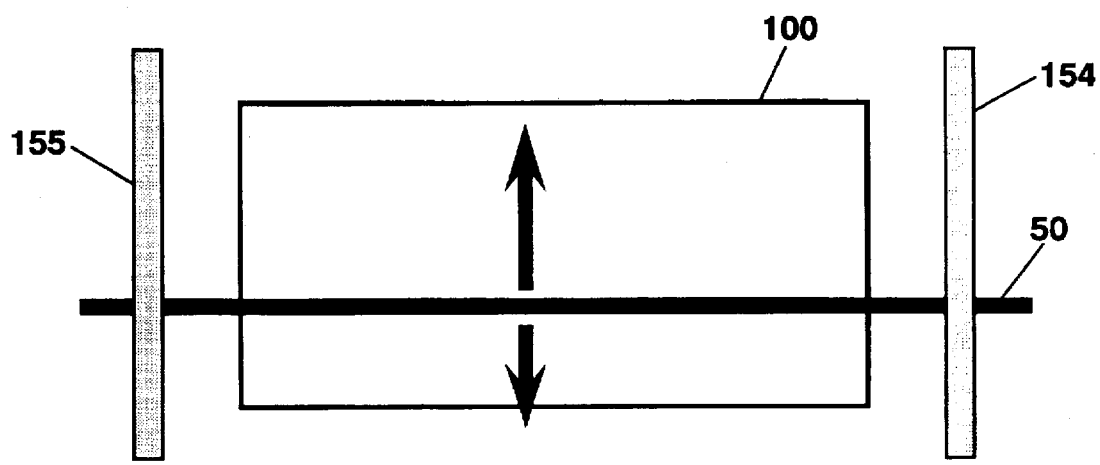
FIG. 4 is a diagrammatic side elevational view of the embodiment shown in FIG. 3.

Referring to FIG. 3 and FIG. 4, conformal line array 50 of acoustic measurement devices 42 is placed along cylindrical structure 100. Only one acoustic measurement device 42 is shown in FIG. 3. With particular reference to FIG. 4, in which acoustic measurement devices 42 are not shown, conformal line array 50 circumferentially traverses structure 100. Conformal line array 50 is moved circumferentially around structure 100 guided by a scanning frame. The scanning frame, which is represented in FIG. 3 and FIG. 4 by circumferential supports 154 and 155, is constructed of an acoustically transparent material, e.g., PVC pipe for underwater acoustic testing.

The movement of conformal ring array 40 or conformal line array 50 can be either automated or manual. If automated, for many embodiments of this invention a stepping motor is a preferable means to move the array, and for some such embodiments it is preferable that the stepping motor be computer-controlled. If manual, a rope and pulley system can be designed to move the array.

The scanning frame shown in FIG. 1 and FIG. 2 is represented by three longitudinal supports, and the scanning frame shown in FIG. 3 and FIG. 4 is represented by two circumferential supports; however, in practicing the present invention the scanning frames can encompass more complex designs, including the suspension of the structure.

Figure 5:
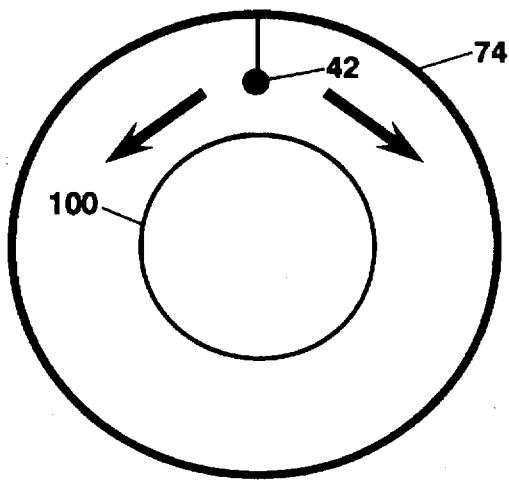
FIG. 5 is a diagrammatic end elevational view of a "stationary conformal ring path" embodiment in accordance with the present invention, wherein the structure is cylindrical.

Instead of a conformal array of acoustic measurement devices 42, measurements may be performed according to this invention by a single acoustic measurement device 42. Reference now being made to FIG. 5, instead of a ring array of acoustic measurement devices, the measurements are performed by a single measurement device which is made to move to different locations in a ring path. Single acoustic measurement device 42 can be moved along stationary surface-conforming ring track 74, which conforms to the surface of cylindrical structure 100 along its circumference. Since device 42 is in a fixed relation to ring track 74, which guides the motion of device 42, device 42 moves in a path which is circumferentially conformal with respect to the surface of structure 100. As shown in FIG. 5, device 42 has one degree of freedom.

Alternatively, surface-conforming ring track 74 can be envisioned in FIG. 5 to be longitudinally movable, rather than stationary, so that device 42 has two degrees of freedom; for example, device 42 can be moved along movable surface-conforming ring track 74 whereby ring track 74 can be moved longitudinally along structure 100 guided by a scanning frame.

Figure 6:
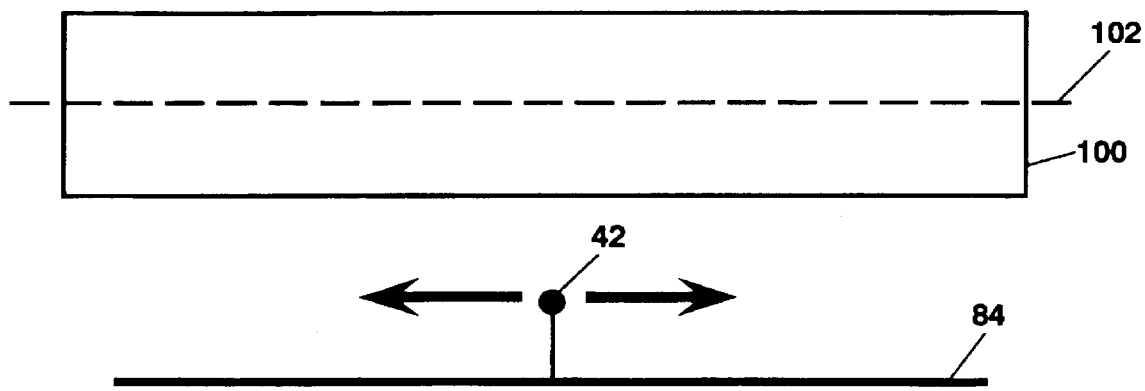
FIG. 6 is a diagrammatic side elevational view of a "stationary conformal line path" embodiment in accordance with the present invention, wherein the structure is cylindrical.

With reference to FIG. 6, acoustic measurement device 42 is moved along stationary surface-conforming line track 84 which conforms to the surface of cylindrical structure 100 along its longitudinal axis 102. Since device 42 is in a fixed relation to line track 84, which guides the motion of device 42, device 42 moves in a path which is longitudinally conformal with respect to the surface of structure 100. As shown in FIG. 6, device 42 has one degree of freedom.

Alternatively, surface-conforming line track 84 can be envisioned in FIG. 6 to be circumferentially movable, rather than stationary, so that device 42 has two degrees of freedom; for example, device 42 can be moved along movable surface-conforming line track 84 whereby line track 84 can be moved circumferentally around structure 100 guided by a scanning frame. Movement of single device 42 can be manipulated by means of a motor (e.g., a computer-controlled stepping motor), not shown in FIG. 5 or FIG. 6.

Figure 7:
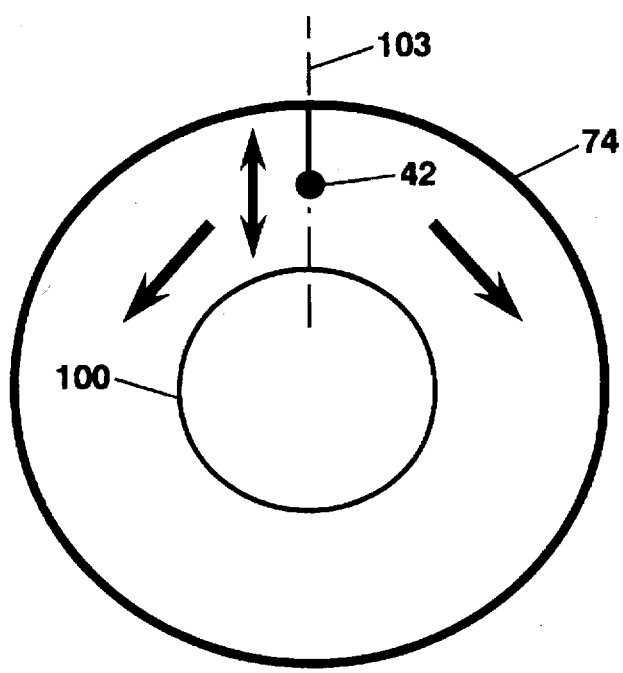
FIG. 7 is a diagrammatic end elevational view of a "radially adjustable stationary conformal ring path" embodiment in accordance with the present invention, wherein the structure is cylindrical.
Figure 8:
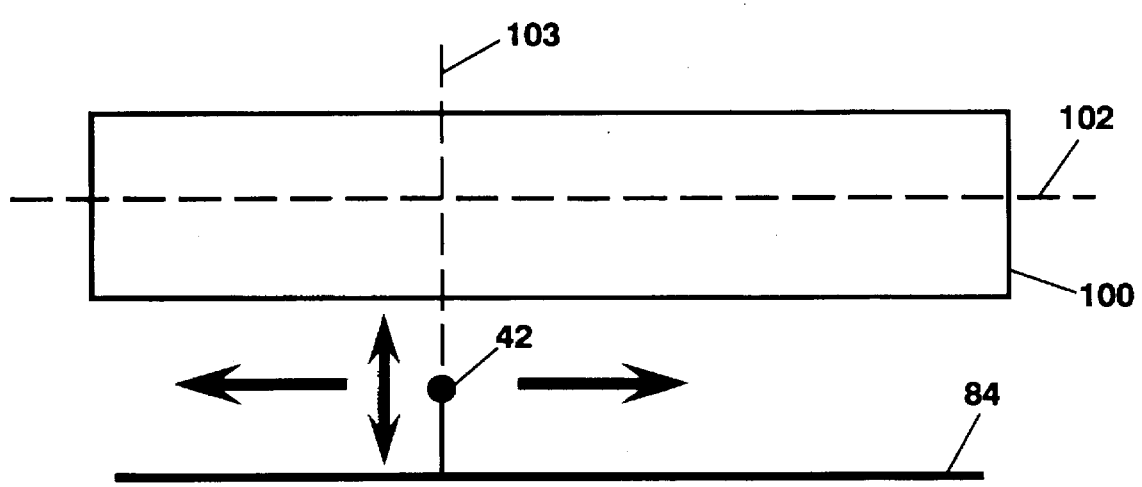
FIG. 8 is a diagrammatic side elevational view of a "radially adjustable stationary conformal line path" embodiment in accordance with the present invention, wherein the structure is cylindrical.

Referring to FIG. 7 and FIG. 8, single acoustic measurement device 42 is shown in each figure to have two degrees of freedom. Device 42 in FIG. 7 can be moved along stationary surface-conforming ring track 74, which conforms to the surface of cylindrical structure 100 along its circumference. The embodiment shown in FIG. 7 may be viewed as an extension of the embodiment shown in FIG. 5 so as to provide radial movability of device 42. Device 42 in FIG. 7 can also be moved radially, i.e., in a path along the surface normal vector represented by dashed line 103.

Alternatively, surface-conforming ring track 74 can be envisioned in FIG. 7 to be movable, rather than stationary, so that device 42 has three degrees of freedom; in the manner discussed above in reference to FIG. 5, device 42 can be moved along movable surface-conforming ring track 74 whereby ring track 74 can be moved longitudinally along structure 100 guided by a scanning frame.

Device 42 in FIG. 8 can be moved along stationary surface-conforming line track 84, which conforms to the surface of cylindrical structure 100 along its longitudinal axis 102. The embodiment shown in FIG. 8 may be viewed as an extension of the embodiment shown in FIG. 6 so as to provide radial movability of device 42. Device 42 in FIG. 8 can also be moved radially, i.e., in a path along the surface normal vector represented by dashed line 103.

Alternatively, surface-conforming ring track 84 can be envisioned in FIG. 8 to be movable, rather than stationary, so that device 42 has three degrees of freedom; in the manner discussed above in reference to FIG. 6, device 42 can be moved along movable surface-conforming track 84 whereby line track 84 can be moved circumferentally around structure 100 guided by a scanning frame.

Figure 9:
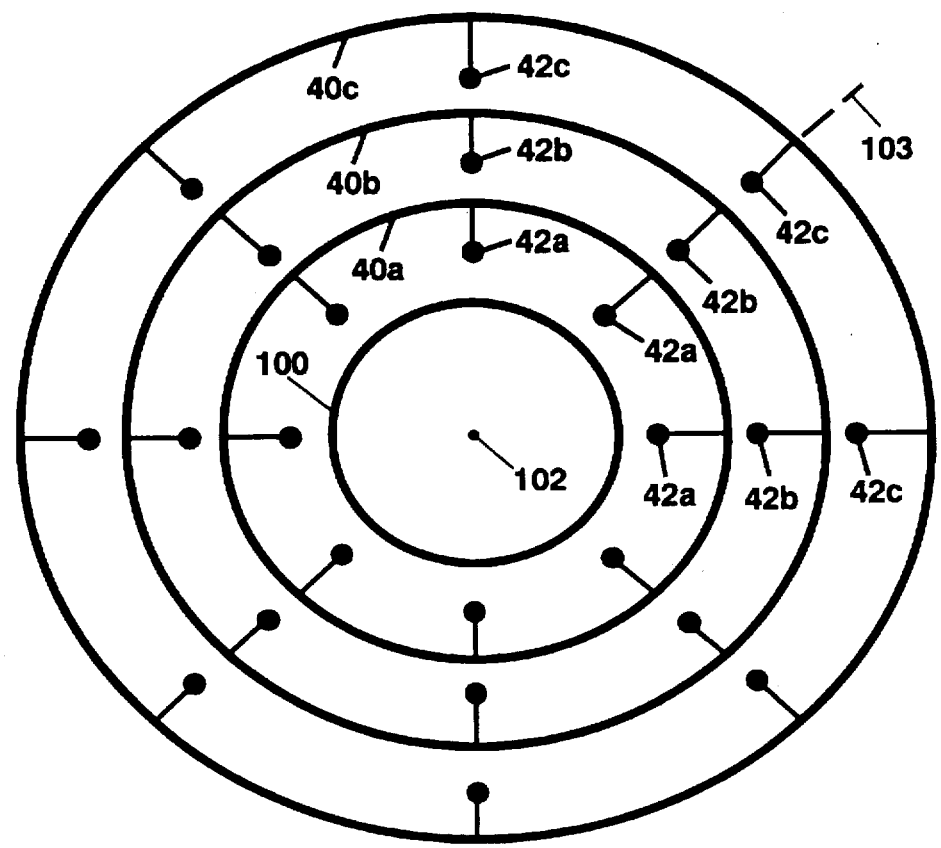
FIG. 9 is a diagrammatic end elevational view of a "multi-tier movable conformal ring array" embodiment in accordance with the present invention, wherein the structure is cylindrical.

Multiple-tier mapping of the acoustic near field of a structure can be provided in accordance with the present invention. Referring to FIG. 9, each tier of acoustic measurement devices 42 has a different radius (i.e., radial distance from longitudinal axis 102, which may be envisioned as the center point for structure 100 as viewed in FIG. 9) and therefore a different distance from the surface (i.e., distance along a surface normal vector) of cylindrical structure 100. The embodiment shown in FIG. 9 may be viewed as an extension to three tiers of the single-tier embodiment shown in FIG. 1 and FIG. 2. Conformal ring array 40a forms the first tier (nearest to structure 100), conformal ring array 40b forms the second tier, and conformal ring array 40c forms the third tier (furthest from structure 100). Additional (or fewer) tiers may be provided as needed. Acoustic measurement devices 42 are aligned along surface normal vectors (e.g., acoustic measurement devices 42a, 42b and 42c are aligned along the surface normal vector represented by dashed line 103.

Figure 10:
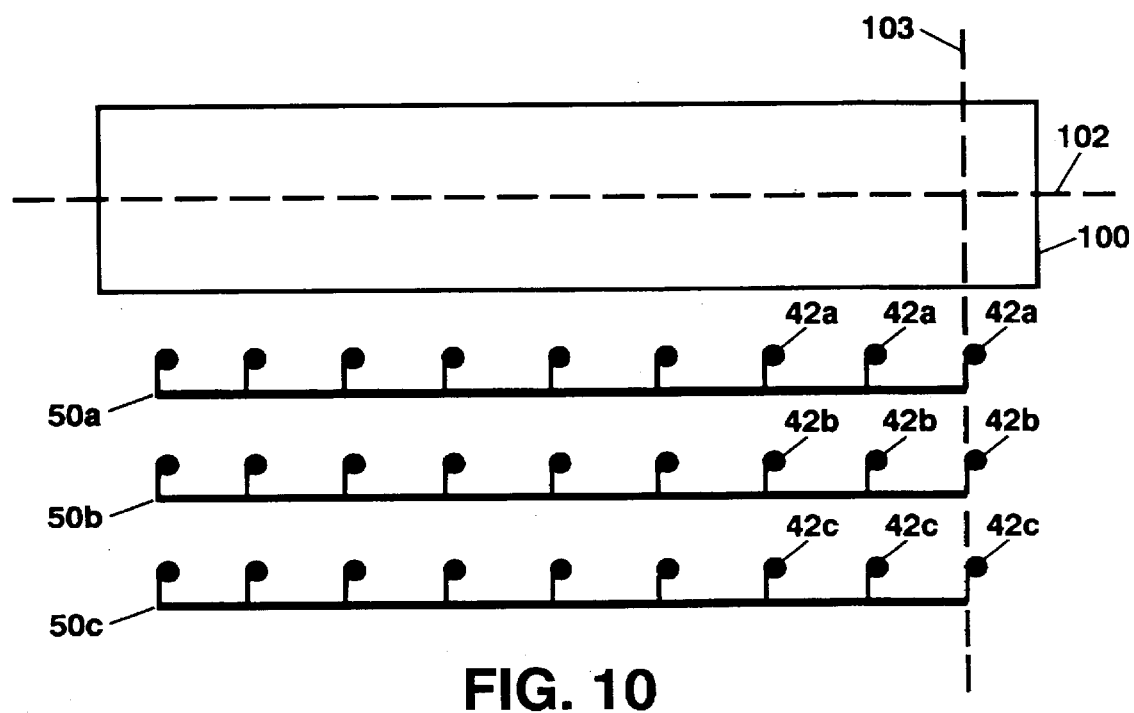
FIG. 10 is a diagrammatic side elevational view of a "multi-tier movable conformal line array" embodiment in accordance with the present invention, wherein the structure is cylindrical.

With reference to FIG. 10, the three tiers are identical or similar, except that each tier of acoustic measurement devices 42 has a different radius (i.e., radial distance from longitudinal axis 102) and therefore a different distance from the surface (i.e., distance along a surface normal vector) of cylindrical structure 100. The embodiment shown in FIG. 10 may be viewed as an extension to three tiers of the single-tier embodiment shown in FIG. 3 and FIG. 4. Conformal line array 50a forms the first tier (nearest to structure 100), conformal line array 50b forms the second tier, and conformal line array 50c forms the third tier (furthest from structure 100). Additional (or fewer) tiers may be provided as needed. Acoustic measurement devices 42 are aligned along surface normal vectors (e.g., acoustic measurement devices 42a, 42b and 42c are aligned along the surface normal vector represented by dashed line 103.

Figure 11:
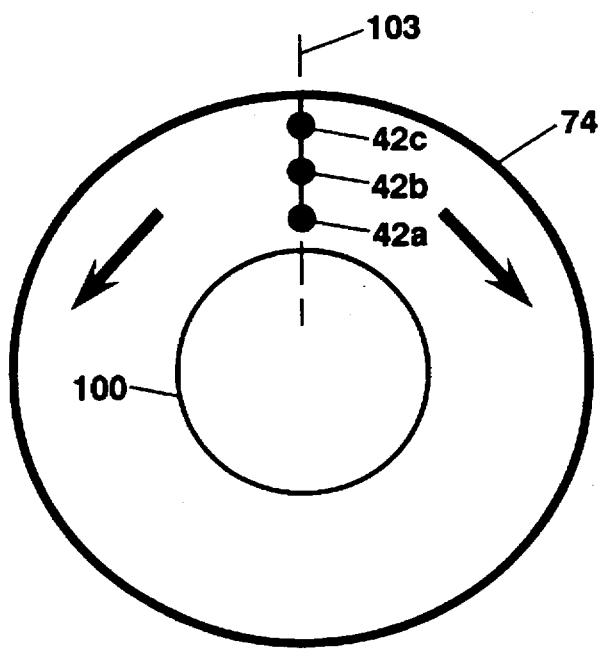
FIG. 11 is a diagrammatic end elevational view of a "multi-device stationary conformal ring path" embodiment in accordance with the present invention, wherein the structure is cylindrical.

Reference now being made to FIG. 11, acoustic measurement devices 42a, 42b and 42c are aligned along the surface normal vector represented by dashed line 103. Each device is aligned along the surface normal vector represented by dashed line 103 and is a unique distance away from the surface of structure 100. The embodiment shown in FIG. 11 may be viewed as an extension to three devices of the single-device embodiment shown in FIG. 5. Acoustic measurement devices 42a, 42b and 42c can be moved as a unit along stationary surface-conforming ring path 74, which conforms to the surface of cylindrical structure 100 along its circumference; as shown for acoustic measurement device 42 in FIG. 5, devices 42a, 42b and 42c have one degree of freedom.

Alternatively, surface-conforming ring path 74 can be envisioned in FIG. 11 to be longitudinally movable, rather than stationary, so that devices 42a, 42b and 42c have two degrees of freedom, as discussed hereinabove in connection with FIG. 5. Alternatively, devices 42a, 42b and 42c can be envisioned to be radially movable as a unit, i.e., along the surface normal vector represented by dashed line 103; as discussed hereinabove in connection with FIG. 7, with such radial movability, devices 42a, 42b and 42c are alternatively provided two degrees of freedom when ring path 74 is stationary, and three degrees of freedom when ring path 74 is longitudinally movable.

Figure 12:
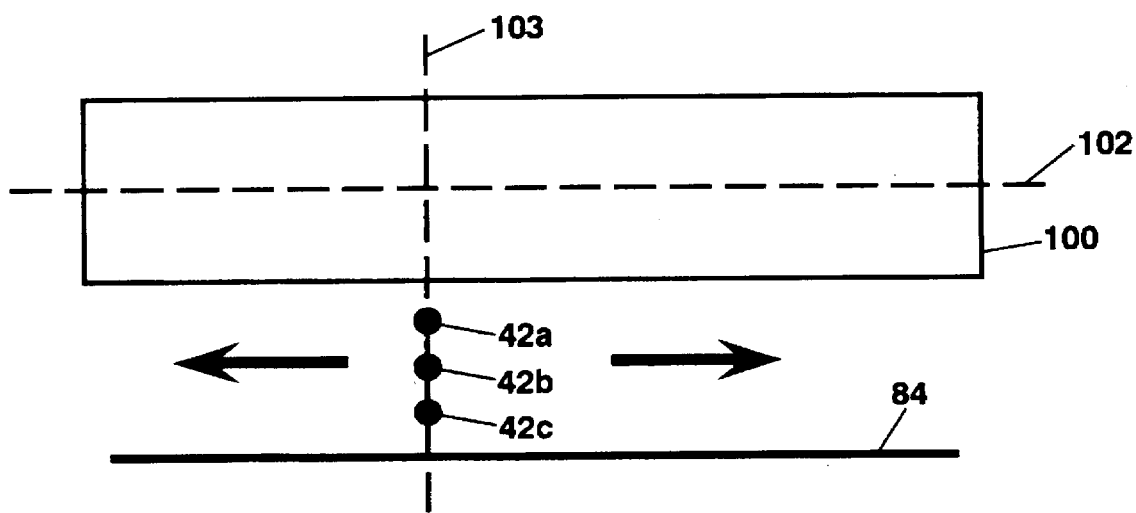
FIG. 12 is a diagrammatic side elevational view of a "multi-device stationary conformal line path" embodiment in accordance with the present invention, wherein the structure is cylindrical.

Referring to FIG. 12, acoustic measurement devices 42a, 42b and 42c are aligned along the surface normal vector represented by dotted line 103. Each device is aligned along the surface normal vector represented by dotted line 103 and is a unique distance away from the surface of structure 100. The embodiment shown in FIG. 12 may be viewed as an extension to three devices of the single-device embodiment shown in FIG. 6. Acoustic measurement devices 42a, 42b and 42c can be moved as a unit along stationary surface-conforming line path 84, which conforms to the surface of cylindrical structure 100 along its longitudinal axis 102; as shown for acoustic measurement device 42 in FIG. 6, devices 42a, 42b and 42c have one degree of freedom.

Alternatively, surface-conforming line path 84 can be envisioned in FIG. 12 to be circumferentially movable, rather than stationary, so that devices 42a, 42b and 42c have two degrees of freedom, as discussed hereinabove in connection with FIG. 6. Alternatively, devices 42a, 42b and 42c can be envisioned to be radially movable as a unit, i.e., along the surface normal vector represented by dotted line 103; as discussed hereinabove in connection with FIG. 8, with such radial movability, devices 42a, 42b and 42c are alternatively provided two degrees of freedom when line path 84 is stationary, and three degrees of freedom when line path 84 is longitudinally movable.

The multi-tier embodiments shown in FIG. 9 and FIG. 10 and the multi-device embodiments shown in FIG. 11 and FIG. 12 are analogous in that devices are radially aligned, i.e., aligned along surface normal vectors, for example as shown in FIG. 9, FIG. 10, FIG. 11 and FIG. 12 by alignment of devices 42a, 42b and 42c along the surface normal vector represented by dotted line 103. It should be understood that radial alignment of acoustic measurement devices such as shown in FIG. 9, FIG. 10, FIG. 11 and FIG. 12, though preferable for some embodiments of the present invention, is not a requirement for practicing the present invention.

The present invention is applicable to structures other than cylinders (such as cones, spheres, prolate spheres, spheroids and ellipsoids) and to structures having circular or non-circular (e.g., elliptical) cross-section. The present invention is also applicable to structures which depart from axial symmetry.

Figure 13:
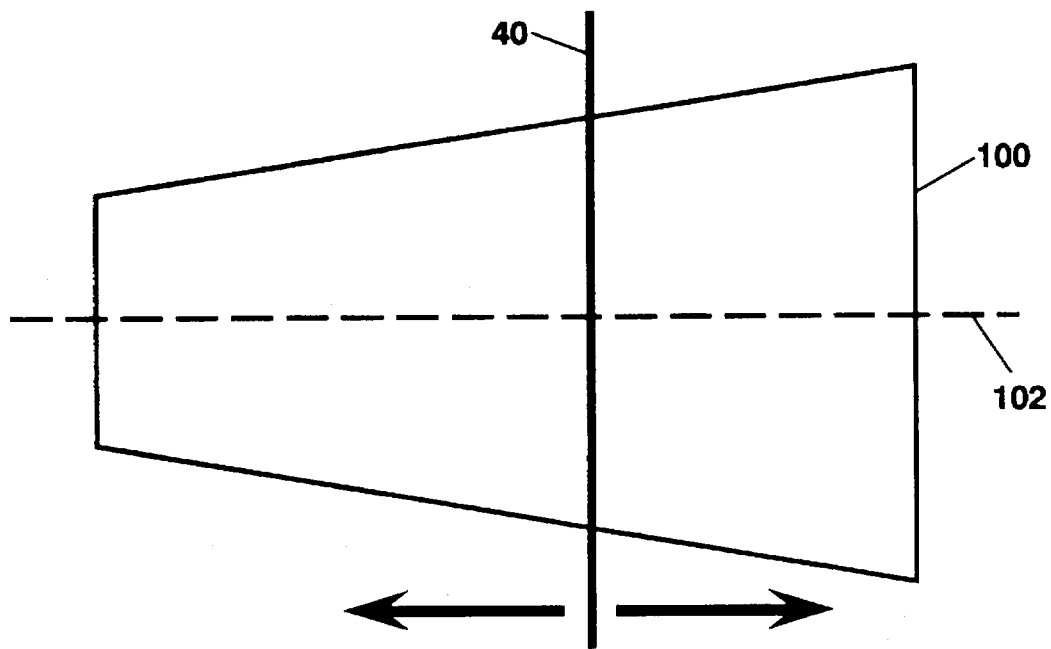
FIG. 13 is a diagrammatic side elevational view of a "movable conformal ring array" embodiment in accordance with the present invention, wherein the structure is conical.

With reference to FIG. 13, conformal ring array 40 of acoustic measurement devices 42 (devices 42 not shown) is placed around conical structure 100. Thus, as discussed hereinabove in connection with FIG. 1 and FIG. 2, a conformal ring array of acoustic measurement devices is placed in the acoustic near field of the structure and conforms to the structure's circumferential surface. As shown in FIG. 13, conformal ring array 40, which circumferentially conforms to the surface of conical structure 100, traverses along longitudinal axis 102.

Figure 14A:
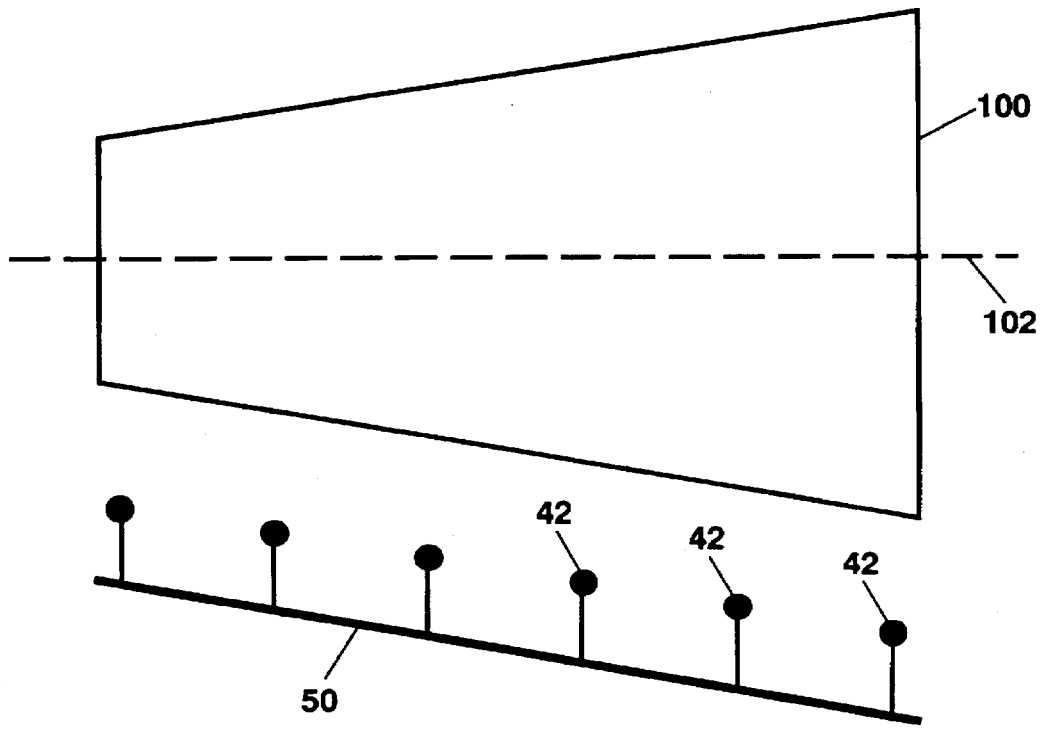
FIG. 14a and FIG. 14b are diagrammatic side elevational views of a "movable conformal line array" embodiment in accordance with the present invention, wherein the structure is conical.
Figure 14B:
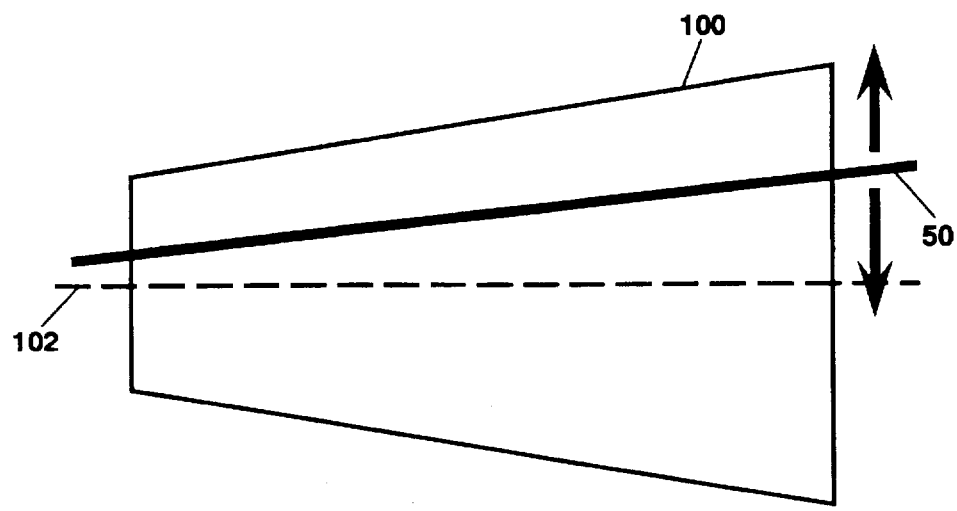

With reference to FIG. 14a and FIG. 14b, conformal line array 50 of acoustic measurement devices 42 is placed along conical structure 100. Thus, as discussed hereinabove in connection with FIG. 3 and FIG. 4, a conformal line array of acoustic measurement devices is placed in the acoustic near field of the structure and conforms to the structure's longitudinal surface. As shown in FIG. 14a and FIG. 14b, conformal line array 50, which longitudinally conforms to the surface of conical structure 100, traverses around longitudinal axis 102.

Figure 15:
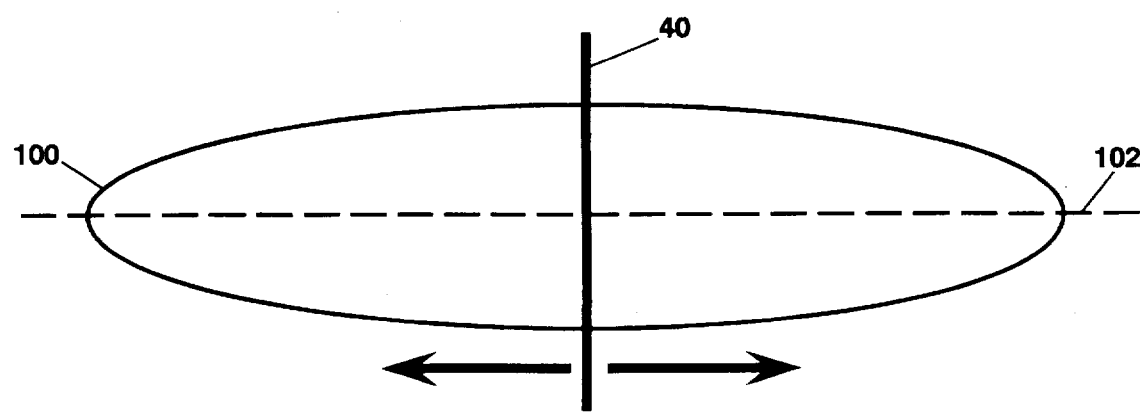
FIG. 15 is a diagrammatic side elevational view of a "movable conformal ring array" embodiment in accordance with the present invention, wherein the structure is prolatedly spheroidal.
Figure 16A:
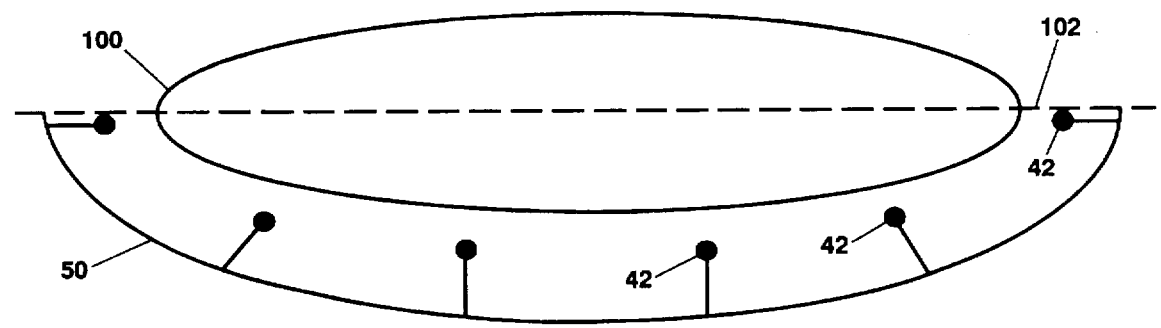
FIG. 16a and FIG. 16b are diagrammatic side elevational views of a "movable conformal line array" embodiment in accordance with the present invention, wherein the structure is prolatedly spheroidal.
Figure 16B:
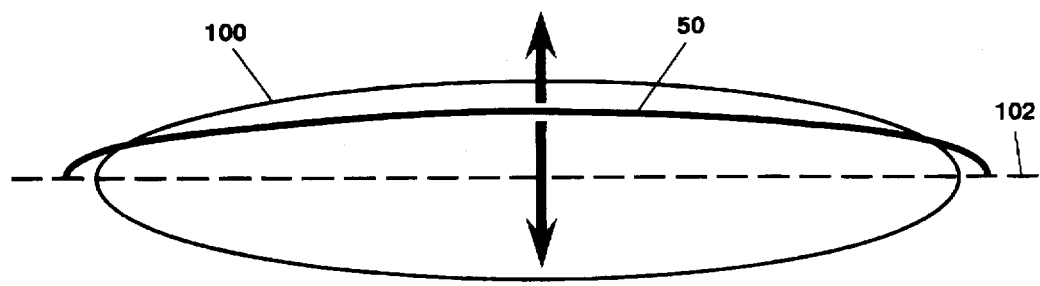
Figure 17:
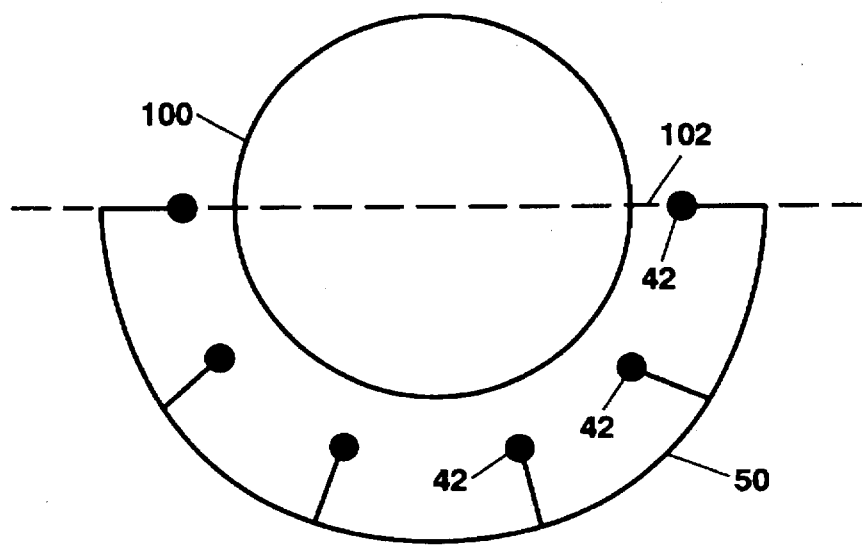
FIG. 17 is a diagrammatic side elevational view of a "movable conformal line array" embodiment in accordance with the present invention, wherein the structure is spherical.

Referring to FIG. 15, conformal ring array 40 circumferentially conforms to the surface of prolate spherical structure 100 and traverses along longitudinal axis 102. Referring to FIG. 16a and FIG. 16b, conformal line array 50 is a curvilinear array of devices 42 which conforms to the surface of prolate spherical structure 100 along longitudinal axis 102 and which traverses around longitudinal axis 102. Referring to FIG. 17, conformal line array 50 is a curvilinear array of devices 42 which conforms to the surface of spherical structure 100 along longitudinal axis 102 and which traverses around longitudinal axis 102.

Alternatively, FIG. 13, FIG. 14a, FIG. 14b, FIG. 15, FIG. 16a, FIG. 16b and FIG. 17 may be envisaged to illustrate various device "path" embodiments of the present invention, which provide one, two or three degrees of freedom, as discussed hereinabove.

Figure 18:
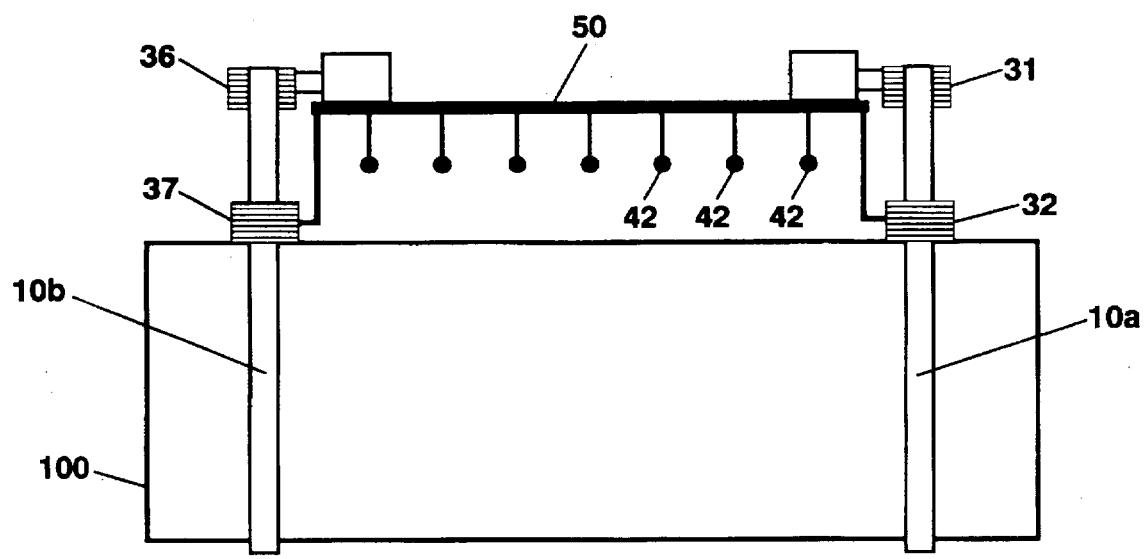
FIG. 18 is a diagrammatic side elevational view of a "belt-driven" embodiment for practicing a "movable conformal line array" in accordance with the present invention.
Figure 19:
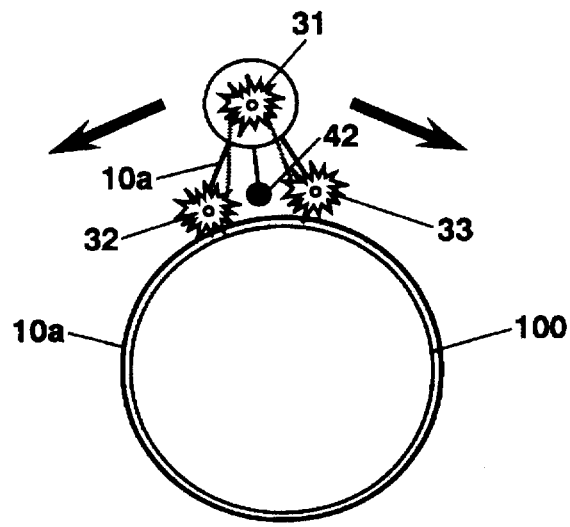
FIG. 19 is a diagrammatic end elevational view of the embodiment shown in FIG. 18.

Reference now being made to FIG. 18 and FIG. 19, conformal line array 50 is rotated circumferentially around cylindrical structure 100. With particular reference to FIG. 18, belts 10a and 10b separately encircle structure 100. Belts 10a and 10b are appropriately toothed, e.g., grooved or notched, and are manufactured from an isolation damping material (e.g., bubbleless rubber). Gears 31 and 36, respectively, step along belts 10a and 10b, respectively, and conformal line array 50 is rotated around structure 100. A computer-controlled stepping motor is a preferable means to turn gears 31 and 36. If an automated implementation is not available, the turning can be performed manually.

With particular reference to FIG. 19, gears 32 and 33 are used for support and to guide belt 10a from structure 100 through gear 31 and back onto structure 100. It may be envisioned that, similarly, gear 37 and another gear, not shown, are used for support and to guide belt 10b from structure 100 through gear 36 and back onto structure 100. Belts 10a and 10b are under sufficient tension that they do not slip when gears 31 and 36 are turned.

In order to precisely rotate conformal line array 50 around structure 100, it may be preferable for some embodiments of this invention that one or more among various adjustments be made with respect to the apparatus shown in FIG. 18 and FIG. 19. To reduce the torque needed by a motor to move conformal line array 50 around structure 100, the motor's drive shaft can be supported on both sides. To alleviate the burden upon the motor's drive shaft to support conformal line array 50, wheels (made of isolation damping material) can be provided which lend such support. Two belts, belts 10a and 10b, are shown in FIG. 18 and FIG. 19; in accordance with this invention, three or more belts can also be appropriately used for rotating conformal line array 50 around structure 100.

Although a "movable conformal line array" embodiment is shown in FIG. 18 and FIG. 19, similar belt-driving principles can be applied for practicing "conformal ring path" embodiments according to this invention. For example, a single acoustic measurement device 42 can be circumferentially conformally moved by implementing a single encircling toothed belt such as belt 10a or belt 10b. Similar belt-driving principles can also be applied for practicing "movable conformal ring array" and "conformal line path" embodiments according to this invention, providing longitudinal motion by implementing one or more longitudinally disposed toothed belts.

According to embodiments of this invention such as shown in FIG. 18 and FIG. 19, a longitudinal line array is rotated circumferentially around the structure using stepping motor means which moves the line array along two toothed belts wrapped around the structure. Although the stepping motor means is not shown in FIG. 18 and FIG. 19, for some such embodiments a first stepping motor can be envisioned to be appropriately coupled with gear 31, and a second stepping motor can be envisioned to be appropriately coupled with gear 36, so that each stepping motor along with the corresponding gear steps along the corresponding belt.

According to embodiments of this invention such as shown in FIG. 20 through FIG. 25, a rack-and-pinion drive mechanism is used to move an acoustic measurement device around the structure. Referring to FIG. 20 through FIG. 25, rack-and-pinion apparatus is utilized for effectuating each of the three possible degrees of movement of acoustic measurement device 42 pursuant to a "path" embodiment. A longitudinal track is utilized for longitudinal movement of device 42 in FIG. 20 and FIG. 21, a circumferential track is utilized for circumferential movement of device 42 in FIG. 22 and FIG. 23, and a radial track is utilized for radial movement of device 42 in FIG. 24 and FIG. 25. Although a single acoustic measurement device 42 is depicted in FIG. 20 through FIG. 25, a plurality of devices 42 may be used, as well, and can be so envisioned in FIG. 20 through FIG. 25.

Figure 20:
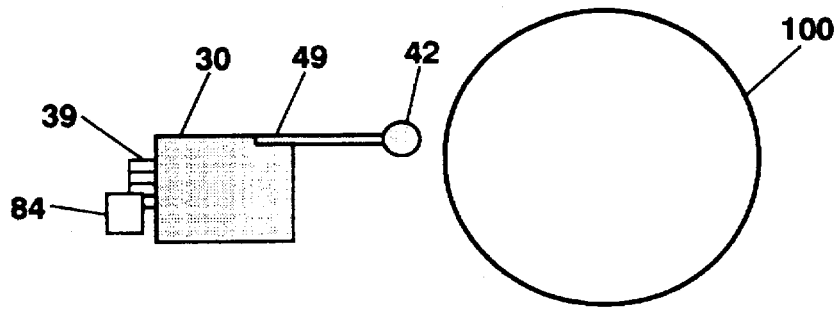
FIG. 20 is a diagrammatic end elevational view of a "rack-and-pinion driven" embodiment for providing longitudinal movability for practicing a "conformal path" in accordance with the present invention.
Figure 21:
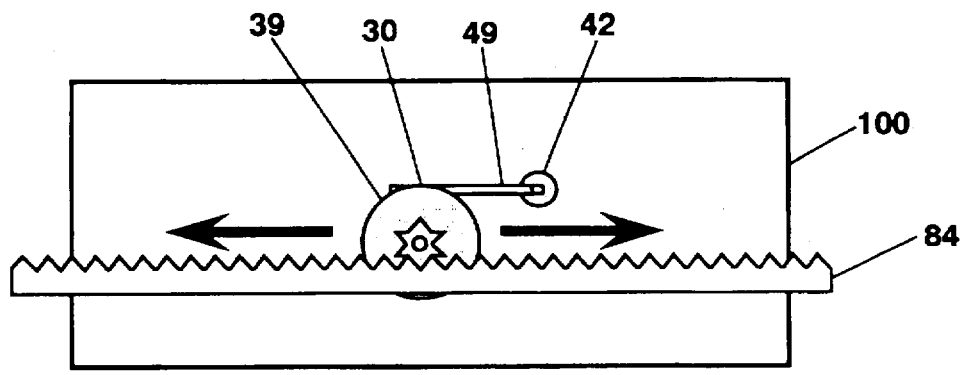
FIG. 21 is a diagrammatic side elevational view of the embodiment shown in FIG. 20.

FIG. 20 and FIG. 21 illustrate the longitudinal scanning sub-system according to this invention. Surface-conforming notched line track 84 is placed longitudinally next to cylindrical structure 100 in the near field. Forming a rack-and-pinion mechanical system, precision stepping motor 30 in contact with line track 84 via gear 39 moves along line track 84 in the longitudinal direction. Acoustic measurement device 42, connected to motor 30 with acoustically transparent support 49, measures the acoustic field next to structure 100. In operation, motor 30 moves device 42 along surface-conforming line track 84 to a new longitudinal position, and device 42 measures the acoustic field. This process of moving device 42 and measuring with device 42 is repeated as is necessary to complete a longitudinal scan of the acoustic near field of structure 100.

Figure 22:
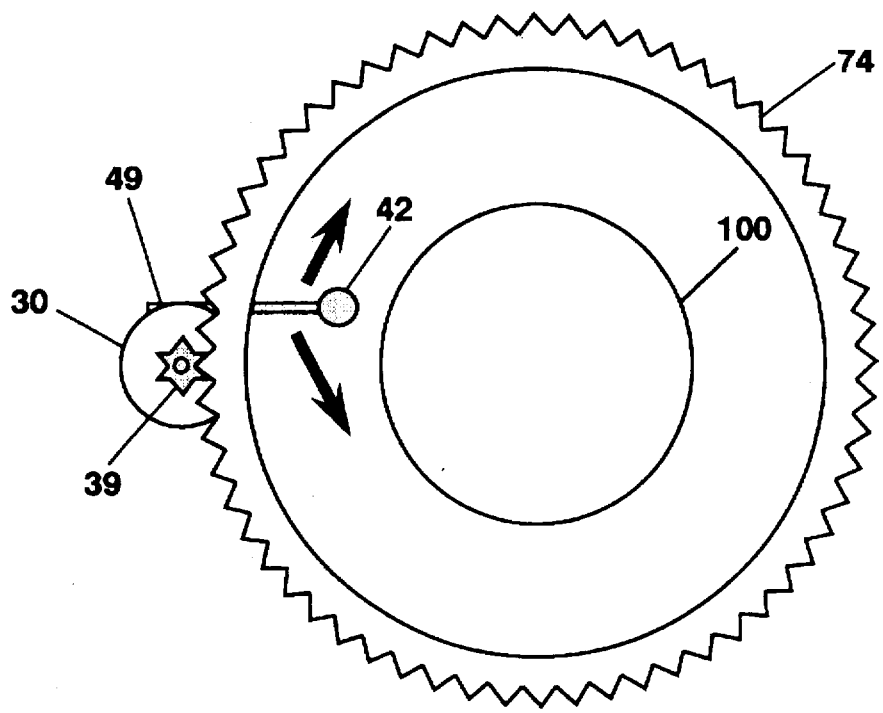
FIG. 22 is a diagrammatic end elevational view of a "rack-and-pinion driven" embodiment for providing circumferential movability for practicing a "conformal path" in accordance with the present invention.
Figure 23:
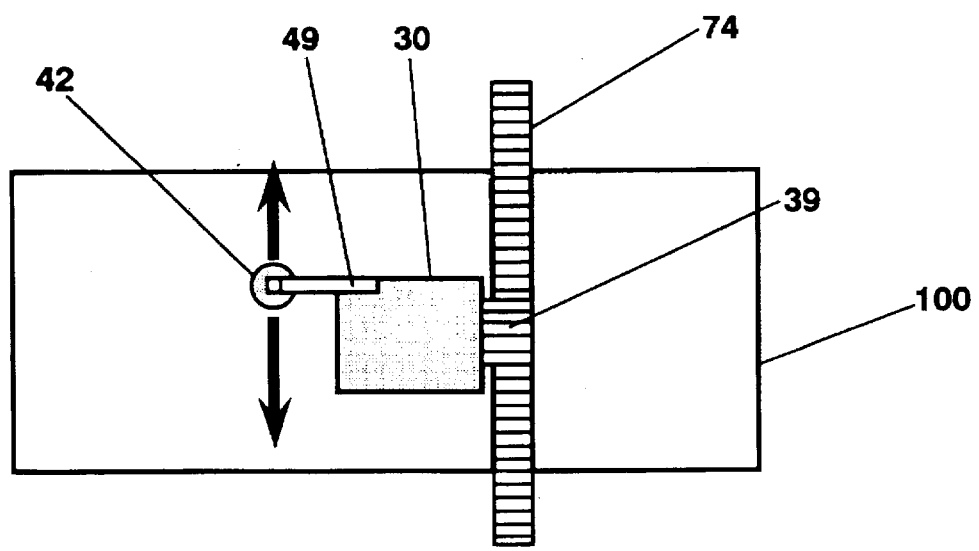
FIG. 23 is a diagrammatic side elevational view of the embodiment shown in FIG. 22.

FIG. 22 and FIG. 23 illustrate the circumferential scanning sub-system according to this invention. Surface-conforming notched ring track 74 is placed circumferentially around cylindrical structure 100 in the near field. Forming a rack-and-pinion mechanical system, precision stepping motor 30 in contact with ring track 74 via gear 39 moves along ring track 74 in the circumferential direction. Acoustic measurement device 42, connected to motor 30 with acoustically transparent support 49, measures the acoustic field next to structure 100. In operation, motor 30 moves device 42 along surface-conforming ring track 74 to a new circumferential position, and device 42 measures the acoustic field. This process of moving device 42 and measuring with device 42 is repeated as is necessary to complete a circumferential scan of the acoustic near field of structure 100.

Figure 24:
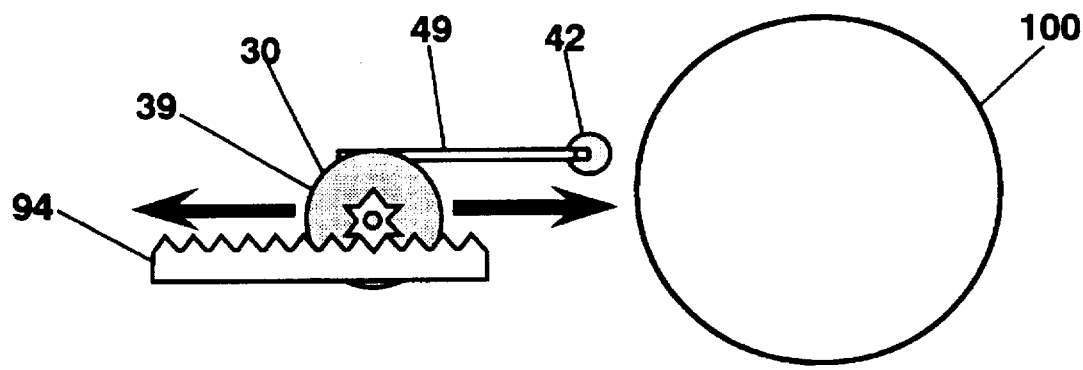
FIG. 24 is a diagrammatic end elevational view of a "rack-and-pinion driven" embodiment for providing radial movability for practicing a "conformal path" in accordance with the present invention.
Figure 25:
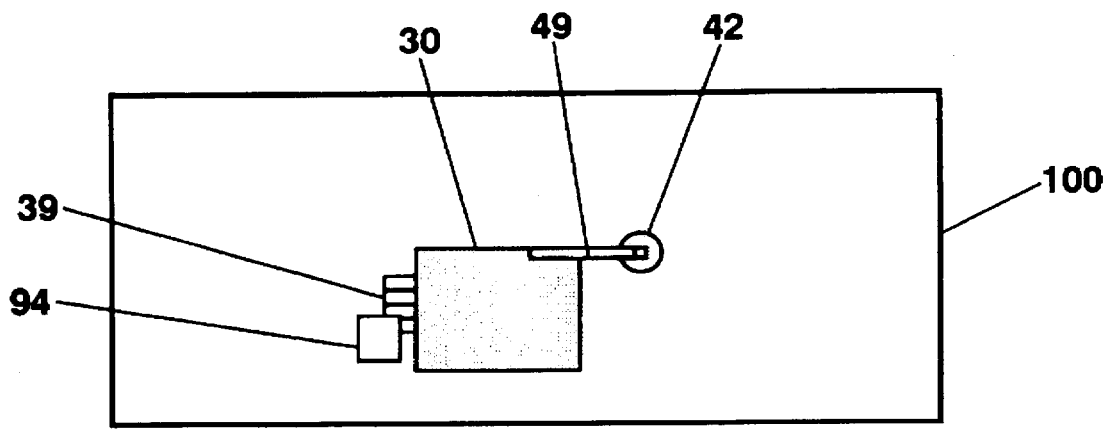
FIG. 25 is a diagrammatic side elevational view of the embodiment shown in FIG. 24.

FIG. 24 and FIG. 25 illustrate the radial scanning sub-system according to this invention. Notched radial track 94 is placed parallel to the radial axis of cylindrical structure 100 in the near field. Forming a rack-and-pinion mechanical system, precision stepping motor 30 in contact with radial track 94 via gear 39 moves along radial track 94 in the radial direction. Since device 42 is in a fixed relation to radial track 94, which guides the motion of device 42, device 42 moves in a path along a surface normal vector such as represented by dotted line 103 in FIG. 7 through FIG. 12. Acoustic measurement device 42, connected to motor 30 with acoustically transparent support 49, measures the acoustic field next to structure 100. In operation, motor 30 moves device 42 to a new longitudinal position along radial track 94, and device 42 measures the acoustic field. This process of moving device 42 and measuring with device 42 is repeated as is necessary to complete a radial scan of the acoustic near field of structure 100.

Although "path" embodiments are shown in FIG. 20 through FIG. 25, similar rack-and-pinion principles can be applied for practicing "conformal array" embodiments according to this invention. For example, a conformal ring array 40 can be longitudinally moved by implementing at least one, and for most embodiments preferably at least two, longitudinally conformal tracks such as line track 84 shown in FIG. 20 and FIG. 21. A conformal line array 50 can be circumferentially moved by implementing at least one, and for most embodiments preferably at least two, circumferentally conformal tracks such as ring track 74 shown in FIG. 22 and FIG. 23. A conformal line array 50 can be radially moved by implementing at least one, and for most embodiments preferably at least two, radial tracks such as radial track 94 shown in FIG. 24 and FIG. 25.

For the sake of clarity, the means for supporting structure 100 and the scanning system are not shown in FIG. 20 through FIG. 25. The structural support is not difficult to implement. For example, many embodiments according to this invention have an acoustically transparent frame which supports both structure 100 and the scanning system.

Any single sub-system or combination of sub-systems among longitudinal and/or circumferential and/or radial movement sub-systems of device 42, with device 42 having one or two or three degrees of movement, can be practiced in accordance with the present invention; one, two or all three of the scanning sub-systems depicted in FIG. 20 through FIG. 25 can be employed, where the number of sub-systems employed corresponds to the degrees of freedom of the scanning system. For the sake of clarity, the combining of two or more sub-systems is not shown in any individual figure among FIG. 20 through FIG. 25. In practicing this invention, the decision as to which single or combination to use may be based upon the type of acoustic information desired.

The combining of sub-systems in accordance with the present invention is not difficult to implement. For instance, the circumferential scanning sub-system of FIG. 22 and FIG. 23 can position the longitudinal scanning sub-system of FIG. 20 and FIG. 21, which in turn can position the radial scanning sub-system of FIG. 24 and FIG. 25, which in turn can position device 42. With this particular combination, the measurement system has three degrees of freedom. Other combinations of sub-systems according to this invention will be apparent to the ordinarily skilled artisan in light of the teachings of this disclosure.

Figure 26:
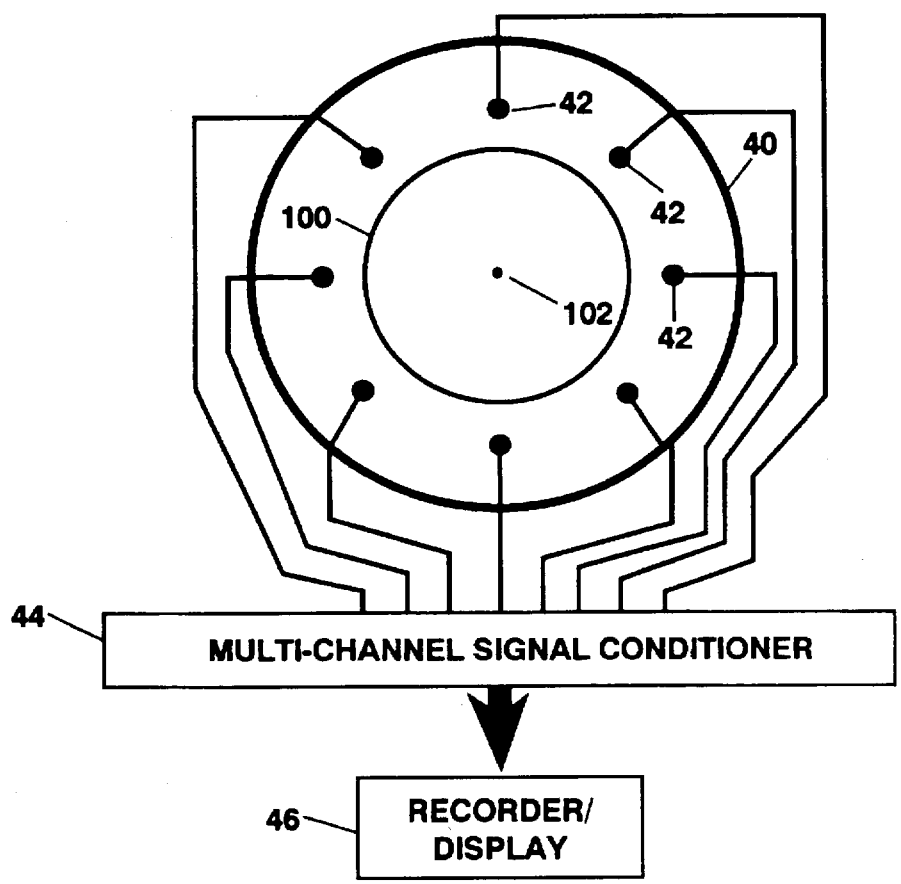
FIG. 26 is a schematic diagrammatic end view illustrating the data acquisition aspect of a "movable conformal ring array" embodiment in accordance with the present invention.
Figure 27:
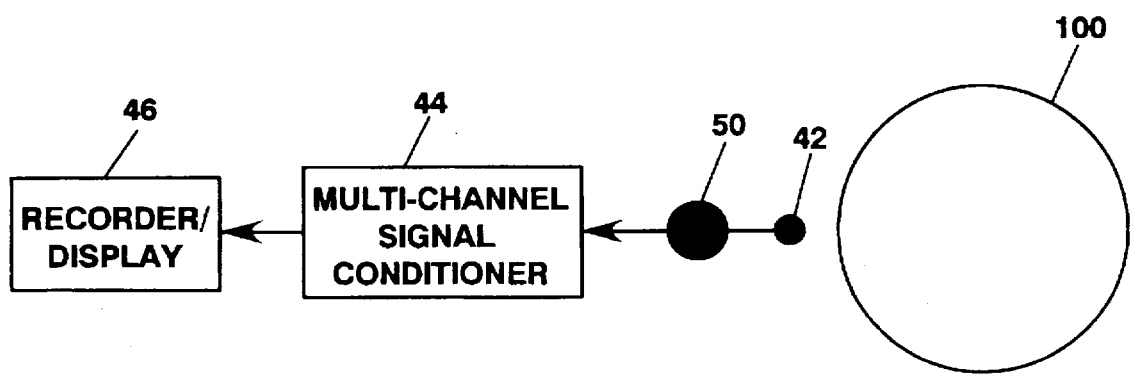
FIG. 27 is a schematic diagrammatic end view illustrating the data acquisition aspect of a "movable conformal line array" embodiment in accordance with the present invention.
Figure 28:
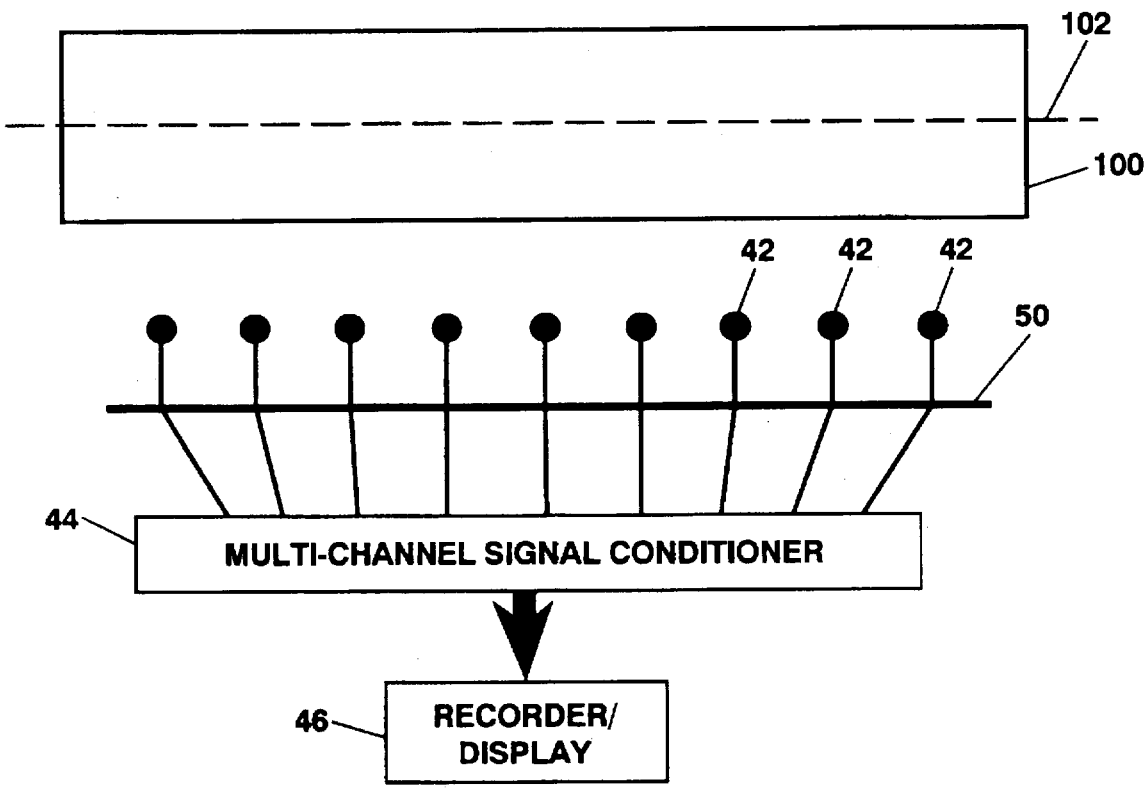
FIG. 28 is a schematic diagrammatic side view illustrating the data acquisition aspect illustrated in FIG. 27.
Figure 29:
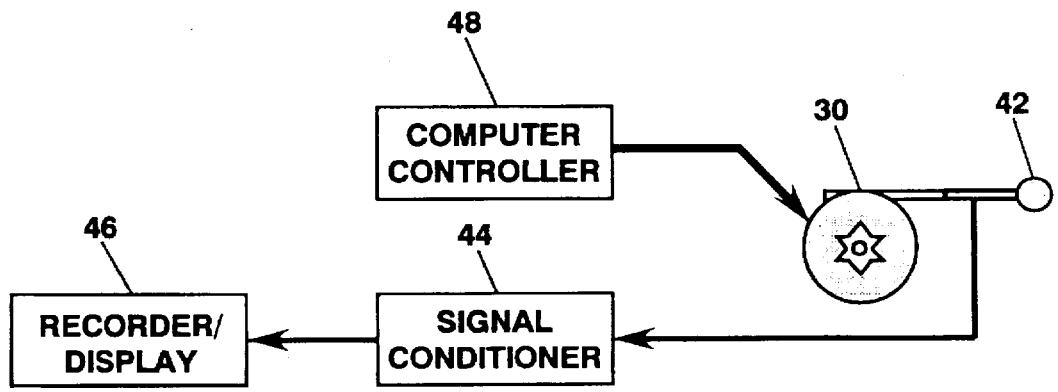
FIG. 29 is a schematic diagrammatic end view illustrating the data acquisition aspect of a "radially adjustable movable conformal path" embodiment in accordance with the present invention.

FIG. 26 through FIG. 29 illustrate data acquisition in accordance with the present invention (scanning frames not shown). In FIG. 26, a conformal ring array of acoustic measurement devices transverses along the longitudinal axis of the structure and measures the acoustic near field. In FIG. 27 and FIG. 28, a conformal line array of measurement devices transverses around the circumference of the structure and measures the acoustic near field. In FIG. 29, rather than using an array of devices to acquire the acoustic measurements, a single acoustic sensor is positioned using a combination of stepping motors; such embodiments of this invention particularly lend themselves to advantageous utilization of the technology of computer-controlled stepping motors for accurately positioning the acoustic sensor.

With particular reference to FIG. 26, conformal ring array 40 is positioned at specific locations along structure 100. With particular reference to FIG. 27 and FIG. 28, conformal line array 50 is positioned at specific locations around structure 100.

Measurement signals are transmitted by the acoustic measurement devices, these measurement signals are conditioned, and information pertaining to the conditioned measurement signals is manifested. Outputs from acoustic measurement devices 42 are fed to multi-channel signal conditioner 44. Functions provided by conditioner 44 may include filtering, analog-to-digital conversion, amplification, etc., according to processes and means well known in the art. The sample data from ring array 40 in FIG. 26, or from line array 50 in FIG. 27 and FIG. 28, may be recorded or displayed on a recorder/display 46 as is well known in the art.

Still particularly referring to FIG. 26, through the repeatable process of measuring the acoustic near field using conformal ring array 40 and longitudinally moving conformal ring array 40 to a new position, the mapping of the acoustic near field for structure 100 is performed. For the mapping process, ring array 40 is moved to a position along longitudinal axis 102 of structure 100, and a measurement of the acoustic near field is acquired. With a large enough test frame, "over-scanning" of the ends of structure 100 can be performed.

With particular reference to FIG. 27 and FIG. 28, through the repeatable process of measuring the acoustic near field using conformal line array 50 and circumferentially moving conformal line array 50 to a new position, the mapping of the acoustic near field for structure 100 is performed. For the mapping process, line array 50 is moved to a position around the circumference of structure 100, and a measurement of the acoustic near field is acquired. With a large enough test frame, "end-region scanning" of the ends of structure 100 can be performed.

Although the belts and gears are not shown in FIG. 27 and FIG. 28, conformal line array 50 in FIG. 27 and FIG. 28 can be visualized to implement belt-and-gear apparatus in accordance with the discussion hereinabove with reference to FIG. 18 and FIG. 19. Conformal line array 50 is rotated to a position around longitudinal axis 102 of structure 100, and a measuring of the acoustic near field is performed. Through the repeatable process of measuring the acoustic near field with line array 50 and rotating line array 50 to a new position, the mapping of the acoustic near field for structure 100 is performed.

With particular reference to FIG. 29, acoustic measurement device 42 is moved by motor 30 to specific locations around structure 100. Sensor 42 in FIG. 29 is representative of the acoustic measurement device employed, and motor 30 is representative of the motors employed in a configuration of the combined longitudinal, circumferential and radial sub-systems as discussed hereinabove with reference to FIG. 20 through FIG. 25. The activity of motor 30 is controlled by computer controller 48.

Measurement signals are transmitted by the acoustic measurement devices, these measurement signals are conditioned, and information pertaining to the conditioned measurement signals is manifested. Acoustic measurements from sensor 42 are fed to multi-channel signal conditioner 44. Functions provided by conditioner 44 in FIG. 29 may include filtering, analog-to-digital conversion, amplification, etc., according to processes and means well known in the art. The sample data from sensor 42 in FIG. 29 may be recorded or displayed on a recorder/display 46 as is well known in the art.

Through the repeatable process of measuring the acoustic near field using sensor 42 and moving sensor 42 to a new position by means of motor 30 (which is representative of a combination of the longitudinal, circumferential and radial sub-systems), the mapping of the acoustic near field for structure 100 is performed. For the mapping process, sensor 42 is moved to a position next to structure 100, and a measurement of the acoustic near field is acquired.

A feedback positioning system can be employed in accordance with this invention, using any of the various sub-systems depicted in FIG. 20 through FIG. 25. As an example, again particularly referring to the radial sub-system depicted in FIG. 24 and FIG. 25, using a high frequency emitter, a high frequency pulse is sent toward structure 100. Using an acoustic measurement device 42 which is a high frequency sensor 42, the reflected pulse is recorded. Considering the speed of sound in the medium and the elapsed time from the release of the pulse to its return, the distance of sensor 42 from the surface of structure 100 can be computed.

Again with reference to FIG. 29, using the computed distance of sensor 42 from the surface of structure 100, computer controller 48 can accurately position sensor 42 through a series of distance measurements. With a feedback positioning system, a non-ideal implementation of the scanning system can be compensated for by appropriately adjusting the position of sensor 42.

In FIG. 20 through FIG. 25, structure 100 is assumed to be cylindrical; however, in accordance with this invention, the sub-systems shown in FIG. 20 through FIG. 25 are applicable to structures which are cylinders and to structures other than cylinders (such as cones, spheres, prolate spheres, spheroids and ellipsoids) and to structures having circular cross-section or non-circular (e.g., elliptical) cross-section. Just as in the description above, the sub-systems are placed in the acoustic near field of the structure and conform to the surface of the structure.

The sub-systems shown in FIG. 20 through FIG. 25 are also applicable to structures which depart from axial symmetry. Implementation of a feedback positioning system such as described hereinabove with reference to FIG. 24, FIG. 25 and FIG. 29 is particularly advantageous for structures having surfaces which are non-uniform, irregular or asymmetrical. With a feedback positioning system, the present invention can be used on shapes departing from axial symmetry by allowing for the positioning of sensor 42 to the appropriate position.

In practice of the present invention, a choice may be required for a given structure as to implementing conformal ring arrayal versus implementing conformal line arrayal. Although implementing both conformal ring arrayal and conformal line arrayal in accordance with this invention for a given structure is possible, it is probably inappropriate or impractical for most applications. Whether to use a conformal ring array of devices or a conformal line array of devices in application to a given structure may depend on the geometry of the structure; whether to use a conformal ring device path or a conformal line device path in application to a given structure may involve similar considerations.

For certain structures, it may be easier to mount a conformal ring array and measure the structure's acoustic near field than to mount a conformal line array and measure the structure's acoustic near field; for other structures, the opposite may be true. For example, it may be easier to use a conformal ring array for a long cylindrical structure. For a prolate spherical structure (which has a constantly varying circumference), for example, it may be easier to use a conformal line array. Hence, depending on the geometry of the structure, one system for scanning the acoustic near field may be more desirable than the other.

Other factors which may militate for or against use of either ring conformity or line conformity include the desired geometry of the measurement surface and the need for measuring the ends of the structure. With respect to the desired geometry of the measurement surface, if the desired measurement surface is cylindrical but less in length than that of the structure, a conformal ring array may be more appropriate than a conformal line array. If the desired measurement surface is the length of the structure but not fully circumferential, a conformal line array may be more appropriate than a conformal ring array.

With respect to the need for measuring the ends of the structure, if the structure is cylindrical with flat ends, a conformal line array with right angled ends to conform to end regions of the cylinder may be more appropriate than a conformal ring array. If an over-scanning of the end region and not a measuring of the end region next to the structure is desired, a conformal ring array may be more appropriate than a conformal line array.

Generally, the practitioner may be presented with more than one viable choice of embodiment of the present invention. The practitioner may need to determine, for example, whether to provide one, two or three degrees of freedom; whether to use conformal ring arrayal, conformal line arrayal and/or device pathway; whether a device path, if used, should be in the longitudinal and/or the circumferential and/or the radial direction; whether to implement manual driving means, or automated driving means such as belt-and-gear driving means or rack-and-pinion driving means; etc. With regard to a decision as to how to embody the present invention for a given application, relevant considerations include, inter alia, the size of the structure, the geometry of the structure, the type of acoustic data desired, the practitioner's budget and the time required to acquire the acoustic data.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. Apparatus for scanning the acoustic near field of a structure having a circumferential surface about its longitudinal axis, comprising:

a frame for said structure;

at least one array of acoustic measurement devices;

means for engaging each said array with respect to said frame so as to be approximately conformal with respect to said surface in the circumferential direction and movable in the longitudinal direction; and means for intermittently driving each said array in the longitudinal direction.

2. Apparatus for scanning the acoustic near field as in claim 1, wherein said frame includes at least one track which is longitudinally adjacent said structure, said means for engaging includes gearing means which meshes with each said track, and said means for intermittently driving includes stepping motor means which turns said gearing means.

3. Apparatus for scanning the acoustic near field as in claim 1, wherein said frame includes at least one toothed belt which longitudinally contacts said structure, said means for engaging includes gearing means which meshes with each said belt, and said means for intermittently driving includes stepping motor means which turns said gearing means.

4. Apparatus for scanning the acoustic near field as in claim 1, further comprising computer means for controlling said means for intermittently driving.

5. Apparatus for scanning the acoustic near field as in claim 1, wherein at least one said device transmits measurement signals, and further comprising:

means for conditioning said measurement signals; and means for manifesting information pertaining to said conditioned measurement signals, said means for manifesting information including means selected from the group consisting of means for recording information and means for displaying information.

6. Apparatus for scanning the acoustic near field as in claim 1, wherein there is a plurality of said arrays, and wherein at least two said arrays are arranged in tiers having different radial distances from said longitudinal axis.

7. Apparatus for scanning the acoustic near field of a structure having a circumferential surface about its longitudinal axis, comprising:

a frame for said structure;

at least one array of acoustic measurement devices;

means for engaging each said array with respect to said frame so as to be approximately conformal with respect to said surface in the longitudinal direction and movable in the circumferential direction; and means for intermittently driving each said array in the circumferential direction.

8. Apparatus for scanning the acoustic near field as in claim 7, wherein said frame includes at least one track which circumferentially surrounds said structure, said means for engaging includes gearing means which meshes with each said track, and said means for intermittently driving includes stepping motor means which turns said gearing means.

9. Apparatus for scanning the acoustic near field as in claim 7, wherein said frame includes at least one toothed belt which circumferentially contacts said structure, said means for engaging includes gearing means which meshes with each said belt, and said means for intermittently driving includes stepping motor means which turns said gearing means.

10. Apparatus for scanning the acoustic near field as in claim 7, further comprising computer means for controlling said means for intermittently driving.

11. Apparatus for scanning the acoustic near field as in claim 7, wherein at least one said device transmits measurement signals, and further comprising:

means for conditioning said measurement signals; and means for manifesting information pertaining to said conditioned measurement signals, said means for manifesting information including means selected from the group consisting of means for recording information and means for displaying information.

12. Apparatus for scanning the acoustic near field as in claim 7, wherein there is a plurality of said arrays, and wherein at least two said arrays are arranged in tiers having different radial distances from said longitudinal axis.

13. Apparatus for scanning the acoustic near field of a structure having a circumferential surface about its longitudinal axis, comprising:

a frame for said structure;

at least one acoustic measurement device;

means for engaging each said device with respect to said frame so as to be movable in a corresponding path which is approximately conformal with respect to said surface in the circumferential direction; and means for intermittently driving each said device in the circumferential direction.

14. Apparatus for scanning the acoustic near field as in claim 13, wherein said frame includes at least one track which circumferentially surrounds said structure, said means for engaging includes gearing means which meshes with each said track, and said means for intermittently driving includes stepping motor means which turns said gearing means.

15. Apparatus for scanning the acoustic near field as in claim 13, wherein said frame includes at least one toothed belt which circumferentially contacts said structure, said means for engaging includes gearing means which meshes with each said belt, and said means for intermittently driving includes stepping motor means which turns said gearing means.

16. Apparatus for scanning the acoustic near field as in claim 13, further comprising computer means for controlling said means for intermittently driving.

17. Apparatus for scanning the acoustic near field as in claim 13, wherein at least one said device transmits measurement signals, and further comprising:

means for conditioning said measurement signals; and means for manifesting information pertaining to said conditioned measurement signals, said means for manifesting information including means selected from the group consisting of means for recording information and means for displaying information.

18. Apparatus for scanning the acoustic near field as in claim 13, further comprising means for engaging at least one said acoustic measurement device with respect to said frame so as to be movable in at least one direction selected from the group of directions consisting of the longitudinal direction and the radial direction.

19. Apparatus for scanning the acoustic near field as in claim 18, wherein said engaging so as to be movable in the longitudinal direction includes engaging whereby said path is movable in the longitudinal direction.

20. Apparatus for scanning the acoustic near field as in claim 13, wherein there is a plurality of said devices, and wherein at least two said devices move each in said corresponding path and move together as a unit.

21. Apparatus for scanning the acoustic near field of a structure having a circumferential surface about its longitudinal axis, comprising:
   a frame for said structure;
   at least one acoustic measurement device;
   means for engaging each said device with respect to said frame so as to be movable in a corresponding path which is approximately conformal with respect to said surface in the longitudinal direction; and
   means for intermittently driving each said device in the longitudinal direction.

22. Apparatus for scanning the acoustic near field as in claim 21, wherein said frame includes at least one track which is longitudinally adjacent said structure, said means for engaging includes gearing means which meshes with each said track, and said means for intermittently driving includes stepping motor means which turns said gearing means.

23. Apparatus for scanning the acoustic near field as in claim 21, wherein said frame includes at least one toothed belt which longitudinally contacts said structure, said means for engaging includes gearing means which meshes with each said belt, and said means for intermittently driving includes stepping motor means which turns said gearing means.

24. Apparatus for scanning the acoustic near field as in claim 21, further comprising computer means for controlling said means for intermittently driving.

25. Apparatus for scanning the acoustic near field as in claim 21, wherein at least one said device transmits measurement signals, and further comprising:
   means for conditioning said measurement signals; and
   means for manifesting information pertaining to said conditioned measurement signals, said means for manifesting information including means selected from the group consisting of means for recording information and means for displaying information.

26. Apparatus for scanning the acoustic near field as in claim 21, further comprising means for engaging at least one said acoustic measurement device with respect to said frame so as to be movable in at least one direction selected from the group of directions consisting of the circumferential direction and the radial direction.

27. Apparatus for scanning the acoustic near field as in claim 26, wherein said engaging so as to be movable in the circumferential direction includes engaging whereby said path is movable in the circumferential direction.

28. Apparatus for scanning the acoustic near field as in claim 21, wherein there is a plurality of said devices, and wherein at least two said devices move each in said corresponding path and move together as a unit.

29. Apparatus for scanning the acoustic near field as in claim 13, further comprising:

means for rendering said path movable in the longitudinal direction; and
   means for intermittently driving said path in the longitudinal direction.

30. Apparatus for scanning the acoustic near field as in claim 29, wherein:
   said frame includes at least one circumferential member selected from the group consisting of a circumferential track and a circumferential toothed belt, said circumferential track circumferentially surrounding said structure, said circumferential toothed belt circumferentially contacting said structure;
   said frame includes at least one longitudinal member selected from the group consisting of a longitudinal track and a longitudinal toothed belt, said longitudinal track being longitudinally adjacent said structure, said longitudinal toothed belt longitudinally contacting said structure;
   said means for engaging each said device includes circumferential gearing means which meshes with each said circumferential member;
   said means for rendering said path movable includes longitudinal gearing means which meshes with each said longitudinal member;
   said means for intermittently driving each said device includes circumferential stepping motor means which turns said circumferential gearing means; and
   said means for intermittently driving said path includes longitudinal stepping motor means which turns said longitudinal gearing means.

31. Apparatus for scanning the acoustic near field as in claim 21, further comprising:
   means for rendering said path movable in the circumferential direction; and
   means for intermittently driving said path in the circumferential direction.

32. Apparatus for scanning the acoustic near field as in claim 31, wherein:
   said frame includes at least one longitudinal member selected from the group consisting of a longitudinal track and a longitudinal toothed belt, said longitudinal track being longitudinally adjacent said structure, said longitudinal toothed belt longitudinally contacting said structure;
   said frame includes at least one circumferential member selected from the group consisting of a circumferential track and a circumferential toothed belt, said circumferential track circumferentially surrounding said structure, said circumferential toothed belt circumferentially contacting said structure;
   said means for engaging each said device includes longitudinal gearing means which meshes with each said longitudinal member;
   said means for rendering said path movable includes circumferential gearing means which meshes with each said circumferential member;
   said means for intermittently driving each said device includes longitudinal stepping motor means which turns said longitudinal gearing means; and
   said means for intermittently driving said path includes circumferential stepping motor means which turns said circumferential gearing means.

* * * * *